United States Patent
Astier et al.

(10) Patent No.: US 12,313,584 B2
(45) Date of Patent: *May 27, 2025

(54) ELECTRIC FIELD-ASSISTED JUNCTIONS FOR SEQUENCING

(71) Applicant: Roche Sequencing Solutions, Inc., Pleasanton, CA (US)

(72) Inventors: Yann Astier, Livermore, CA (US); Zsolt Majzik, Dublin, CA (US); Flint Mitchell, Menlo Park, CA (US); Juraj Topolancik, Redwood City, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1008 days.

This patent is subject to a terminal disclaimer.

(21) Appl. No.: 17/286,366

(22) PCT Filed: Jun. 19, 2019

(86) PCT No.: PCT/EP2019/066199
§ 371 (c)(1),
(2) Date: Apr. 16, 2021

(87) PCT Pub. No.: WO2020/078595
PCT Pub. Date: Apr. 23, 2020

(65) Prior Publication Data
US 2021/0381997 A1    Dec. 9, 2021

Related U.S. Application Data

(60) Provisional application No. 62/748,223, filed on Oct. 19, 2018.

(51) Int. Cl.
*G01N 27/327* (2006.01)
*C12Q 1/6825* (2018.01)
(Continued)

(52) U.S. Cl.
CPC ....... *G01N 27/3272* (2013.01); *C12Q 1/6825* (2013.01); *C12Q 1/6869* (2013.01);
(Continued)

(58) Field of Classification Search
CPC . G01N 27/3272; G01N 27/3275–3276; G01N 27/3278; G01N 27/48;
(Continued)

(56) References Cited

U.S. PATENT DOCUMENTS

| 11,718,870 B2 * | 8/2023 | Astier ................. C12Q 1/6869 435/6.11 |
| 2005/0100930 A1 * | 5/2005 | Wang ..................... B82Y 15/00 436/526 |

(Continued)

FOREIGN PATENT DOCUMENTS

| CA | 2695834 A1 | 9/2010 |
| CN | 104254771 A | 12/2014 |

(Continued)

OTHER PUBLICATIONS

International Search Report and Written Opinon from PCT Appln. PCT/EP2019/066199 mailed Jul. 31, 2019; 13 pages.

*Primary Examiner* — James Lin
*Assistant Examiner* — Vivian A Tran
(74) *Attorney, Agent, or Firm* — Kilpatrick Townsend and Stockton LLP

(57) ABSTRACT

Molecules may be analyzed (e.g., sequencing of nucleic acid molecules) by tunneling recognition at a tunneling junction. Embodiments of the present invention may allow detecting individual nucleotides and the sequencing of a nucleic acid molecule using a tunneling junction. By labeling a specific 5 nucleotide with a moiety, tunneling junctions may generate a signal with a suitable signal-to-noise ratio. An electric field may be applied to move the nucleic acid molecule and the (Continued)

moiety close to the tunneling junction so that a current may travel through the moiety. Because a single nucleotide can be detected with a signal with a suitable signal-to-noise ratio resulting from the tunneling current passing through 10 the moiety, embodiments of the present invention may allow for fast detection of nucleotides using a tunneling current.

10 Claims, 23 Drawing Sheets

(51) Int. Cl.
*C12Q 1/6869* (2018.01)
*C12Q 1/6874* (2018.01)
*G01N 33/487* (2006.01)

(52) U.S. Cl.
CPC ....... *C12Q 1/6874* (2013.01); *G01N 27/3275* (2013.01); *G01N 27/3276* (2013.01); *G01N 27/3278* (2013.01); *G01N 33/48721* (2013.01)

(58) Field of Classification Search
CPC .. G01N 33/48721; C12Q 1/68; C12Q 1/6818; C12Q 1/6825; C12Q 1/6844; C12Q 1/6869; C12Q 1/6874; C12Q 2565/631; C12Q 2565/543
See application file for complete search history.

(56) References Cited

U.S. PATENT DOCUMENTS

| 2014/0134616 | A1 | 5/2014 | Davis et al. |
| 2014/0147835 | A1* | 5/2014 | Astier ................. C12Q 1/6869 435/5 |
| 2016/0187282 | A1 | 6/2016 | Gardner et al. |
| 2017/0342480 | A1 | 11/2017 | Astier |
| 2018/0237850 | A1* | 8/2018 | Mandell ............. G01R 33/1276 |
| 2018/0238824 | A1 | 8/2018 | Lee et al. |
| 2019/0169684 | A1* | 6/2019 | Oldham ............... C12Q 1/6869 |

FOREIGN PATENT DOCUMENTS

| CN | 104955958 A | 9/2015 |
| CN | 107075579 A | 8/2017 |
| CN | 107250780 A | 10/2017 |
| CN | 107810411 A | 3/2018 |
| CN | 108291902 A | 7/2018 |
| CN | 108593927 A | 9/2018 |
| JP | 2021528065 A | 10/2021 |
| WO | 2013/154999 A2 | 10/2013 |
| WO | 2014/160036 A1 | 10/2014 |
| WO | 2016/010975 A2 | 1/2016 |
| WO | 2016/100749 A1 | 6/2016 |
| WO | 2016/183218 A1 | 11/2016 |
| WO | 2017/001484 A1 | 1/2017 |
| WO | 2017/050719 A1 | 3/2017 |
| WO | 2017/207613 A1 | 12/2017 |
| WO | 2018/065299 A1 | 4/2018 |
| WO | 2019/243421 A1 | 12/2019 |

* cited by examiner

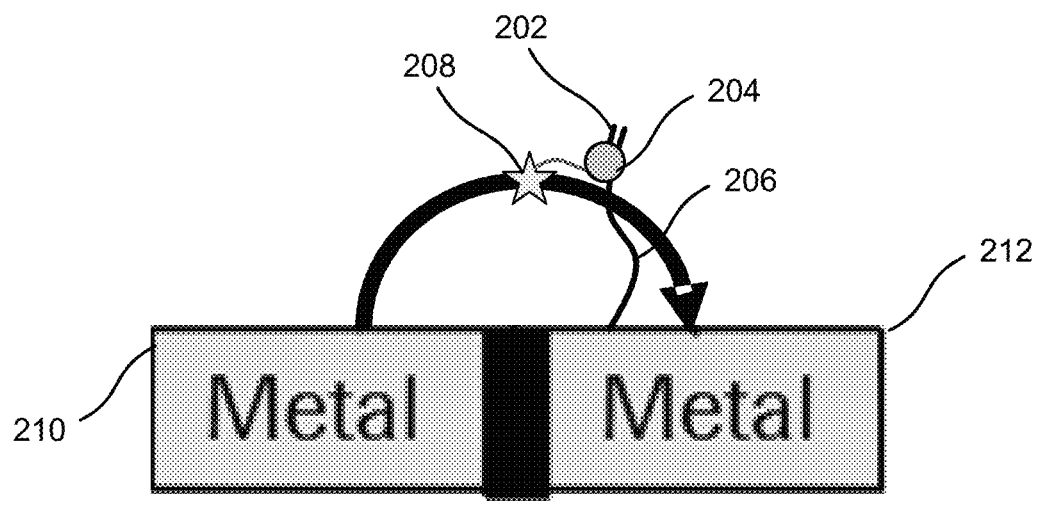
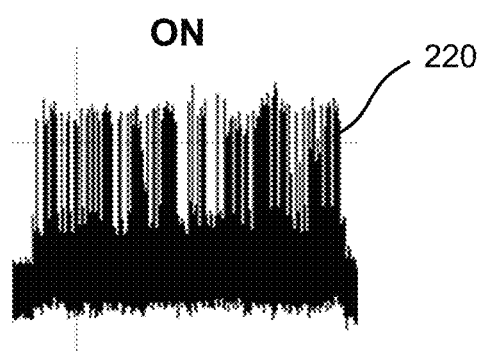
FIG. 2A

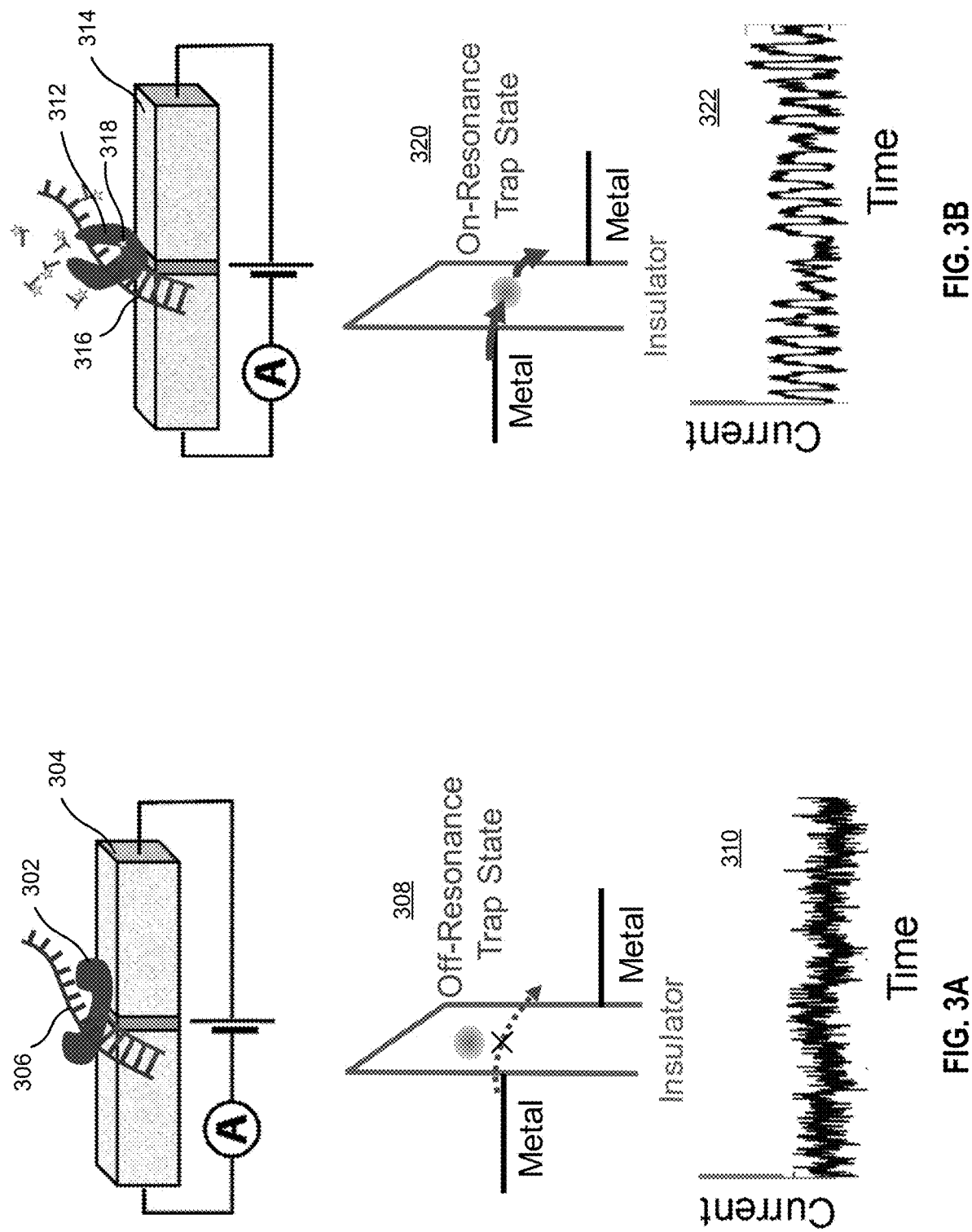

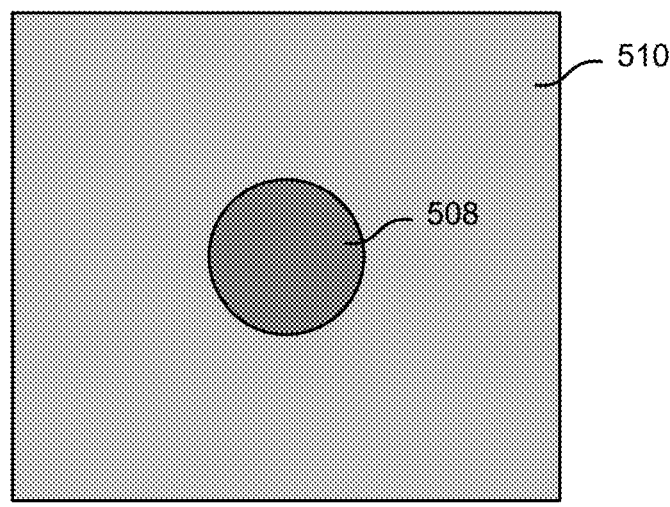
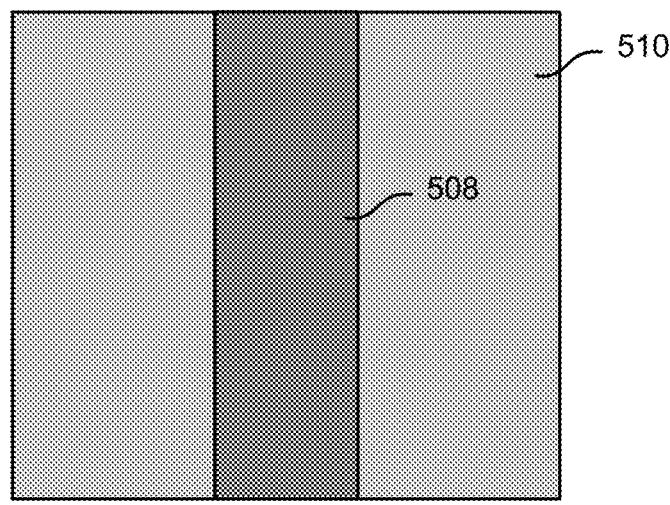
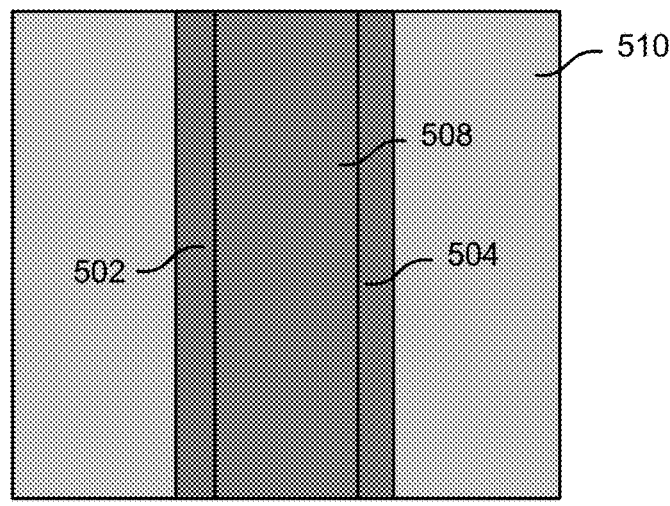
FIG. 5G

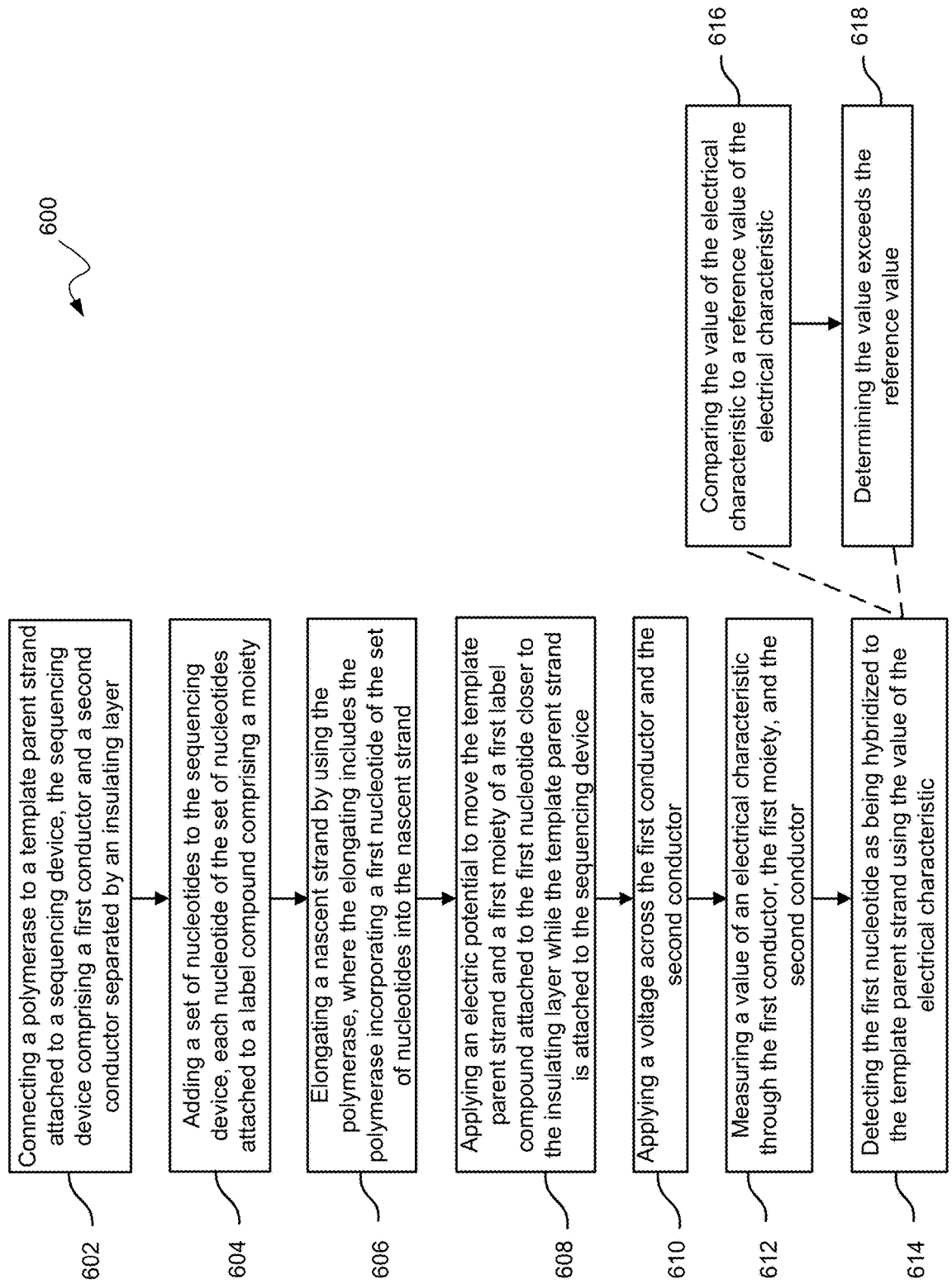

ELECTRIC FIELD-ASSISTED JUNCTIONS FOR SEQUENCING

The present patent application is a US National Phase Application under Section 371 of PCT/EP2019/066199, filed Jun. 19, 2019, which claims priority to U.S. Provisional Patent Application 62/748,223 filed Oct. 19, 2018. This application is related to U.S. Provisional Patent Application No. 62/688,257, entitled "TUNNELING JUNCTIONS FOR SEQUENCING," filed Jun. 21, 2018, and U.S. Provisional Application No. 62/654,894, entitled "FABRICATION OF TUNNELING JUNCTIONS WITH NANOPORES FOR MOLECULAR RECOGNITION," filed Apr. 9, 2018. The entire contents of all of these are incorporated herein by reference for all purposes.

BACKGROUND

Technologies for analyzing single molecules (e.g. nucleic acids) include tunneling junction devices that have a sub-molecular sized gap between two conducting layers. Tunneling junctions use tunneling recognition. Tunneling recognition is based on placing a molecule or a portion of a molecule (e.g., a nucleotide of a nucleic acid) between conducting layers. When the molecule or the portion of the molecule contacts or is sufficiently close to both layers, the orbitals of the molecule or portion of the molecule will allow electrons to transfer from one layer to the other, creating a tunneling current. The tunneling current can be analyzed to identify the molecule or the portion of the molecule.

To identify portions of the molecule, such as nucleotides, dimensions of the gap would normally have to be on the order of nanometers, including less than 2 nm, or even sub-nanometer. Creating a gap of this small size requires precise and expensive techniques. Reducing dimensions of the tunneling junction may also make contact of the molecule less frequent and for a shorter duration. Additionally, such a small gap size may cause shorts and may lead to a high background tunneling current.

Therefore, improvements in the design and manufacturability of tunnel junctions used in chemical and biological detection and processes involving the devices are still needed. Design and manufacturability improvements should not come at the expense of accurate and precise analysis. These and other issues are addressed by the technology described in this document.

BRIEF SUMMARY

Embodiments of the present invention may allow for the analysis of molecules (e.g., sequencing of nucleic acid molecules) by tunneling recognition at a tunneling junction. The tunneling junction may be an electrical tunneling junction or a magnetic tunneling junction. Embodiments of the present invention may allow detecting individual nucleotides, and thus accurate sequencing of a nucleic acid using a tunneling junction may be achieved. By labeling a specific nucleotide with a moiety, tunneling junctions may generate a binary signal that is clear with a suitable signal-to-noise ratio. The tunneling recognition can use a tunneling current that is mostly through the moiety rather than mostly through the nucleotide or a portion of the molecule of interest. An electric field can be applied to move the molecule and the moiety closer to the tunneling junction. In this manner, the moiety is in a position close enough for current to pass through the moiety.

The tunneling junction devices may focus on reading a single nucleotide at a time. Multiple and identical copies of a single-stranded nucleic acid molecule may be attached to the tunneling junction at one end of the molecules. The single-stranded nucleic acid molecules may be attached to an adhesion layer, which may be disposed on an electrode of the tunneling junction device. The single-stranded nucleic acid molecules may serve as template strands. Polymerases may be connected to the template strands and may be used to synthesize double-stranded DNA molecules using the template strands. A single type of nucleotide (e.g., A nucleotides) may be labeled with a moiety and introduced to the device. The nucleotide is incorporated into the DNA molecule if it is complementary to the template strand at a current position. The device may be washed of excess free nucleotides. An electric field may be applied using a field electrode to push the DNA molecule and the moiety toward the tunneling junction. If the nucleotide is added to the DNA molecule, then the moiety may cause a current signal in the tunneling junction. If the nucleotide is not added to the DNA molecule, then the current may be near zero. The moiety may then be removed. The next type of labeled nucleotide can be introduced to the device, and the process can be repeated. The current signal generated by the moiety may be a higher current than a background current through the nucleotide itself.

Because a single nucleotide can be detected with a signal having a suitable signal-to-noise ratio resulting from the tunneling current passing through the moiety, embodiments of the present invention may allow for fast detection of nucleotides using a tunneling current. By detecting current through the moiety rather than the nucleotide itself, the dielectric in the tunneling junction may be thicker than the size of a single nucleotide. Hence, the tunneling junctions can be manufactured more easily, more cheaply, and more quickly.

The tunneling junction devices may be manufactured with semiconductor processing techniques. The read time for detecting a nucleotide may approach or be equivalent to read times with flash drives. Incorporating a plurality of tunneling junctions into a single sequencing device may allow for multiplexing. Embodiments of the present invention may allow for a number of tunneling junctions similar to the number of tunneling junctions in a flash drive. In other words, billions of tunnel junctions could be incorporated in a device the size of a flash drive (an area on the order of a square centimeter). A highly multiplexed system may enable rapid and accurate sequencing.

A better understanding of the nature and advantages of embodiments of the present invention may be gained with reference to the following detailed description and the accompanying drawings.

BRIEF DESCRIPTION OF THE DRAWINGS

FIGS. 2A and 2B show diagrams of the tunneling current through a nucleotide with and without a moiety according to embodiments of the present invention.

FIGS. 3A and 3B show the tunneling current response to a nucleotide with and without a moiety according to embodiments of the present invention.

FIGS. 5A-5H illustrate configurations used in determining a nucleic acid sequence according to embodiments of the present invention.

FIG. 6 illustrates steps of determining a nucleic acid sequence with an electrical tunneling junction according to embodiments of the present invention.

TERMS

Figure 1:
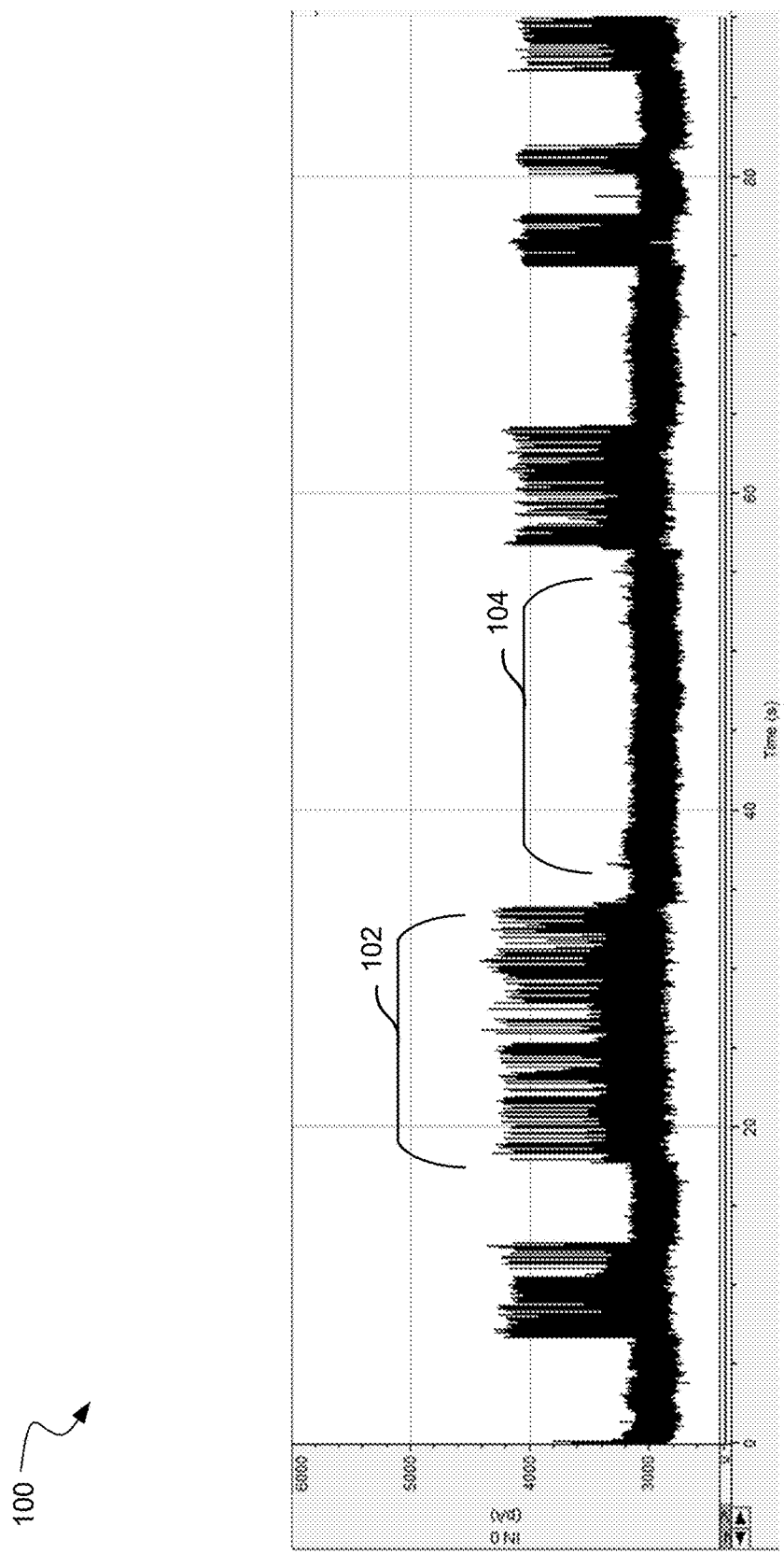
FIG. 1 shows a graph of Random Telegraphic Noise (RTN) according to embodiments of the present invention.

The term "contacting" may refer to bringing one object in proximity to another object such that electrons may tunnel from one object through the other object. At a subatomic level, two objects may never physically touch each other as repulsive forces from electron clouds in the objects may prevent the objects from coming into closer proximity.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid. Examples of such analogs may include, without limitation, phosphorothioates, phosphoramidates, methyl phosphonates, 2-O-methyl ribonucleotides, locked nucleic acids (LNAs), peptide nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "oscillate" may refer to the motion of an object in a fluid as a result of Brownian motion or other forces. An object may oscillate without active intervention by a person or a machine. In some cases, an object may oscillate as a result of an applied electric field or a pressure-driven flow.

The term "moiety" may include a functional group, as the technical term is used in chemistry. In addition, moiety may also refer to an atom or group of atoms bonded together that may form part of a larger compound. Moieties may include magnetic nanoparticles.

Directional terms such as "above" or "on top of" for semiconductor processing layers and steps may use a reference frame where these terms designate a position farther away from a plane defined by a surface of the substrate. The "bottom" may be the underside of a substrate or toward the underside of the substrate. One of skill would understand that even if a substrate is processed upside-down, the "bottom" of a layer may still refer to a side of the layer closest to the underside or non-processed side of a substrate.

The term "electrical characteristic" may be understood to refer to any property related to an electrical circuit. Electrical characteristic may refer to voltage, current, resistance, impedance, inductance, or capacitance, and time variations thereof (e.g., current frequency).

DETAILED DESCRIPTION

Tunneling recognition is a technique used to identify molecules or portions of molecules (e.g., a nucleic acid). A tunneling junction may include an electrical tunneling junction or a magnetic tunneling junction. An electrical tunneling junction may include two conductors sandwiching an insulating layer. When a molecule or a portion of the molecule contacts both conductors or is sufficiently close to both conductors, the current tunneling from one conductor to the other changes. The molecule or portion of the molecule may change the amplitude of the current by inducing direct conduction or trap-assisted tunneling.

A magnetic tunneling junction may include two ferromagnetic materials sandwiching an insulating layer. When a magnetic nanoparticle is close to the ferromagnetic materials, the relative orientation of the magnetic domains changes and the current tunneling from one conductor to the other changes. The amount of tunneling current depends on the orientation of the magnetization (i.e., the spin) of the ferromagnetic materials. The current for ferromagnetic materials having the same spin (i.e., being parallel) is higher than two ferromagnetic materials having opposite spin (i.e., being antiparallel).

With either junction, the tunneling current may vary depending on the identity of the molecule or portion of the molecule that contacts both conductors and how much the molecule oscillates between contacting and not contacting the conductors. If the current through only a single nucleotide of a nucleic acid is to be measured, the insulating layer would typically have to be less than the size of a nucleotide so that the nucleotide can contact both conductors across the insulating layer.

However, even a thickness of 1 nm is about the size of three nucleotides, which can cause problems for detection of a single nucleotide. Even when the thickness of the insulating layer is on the order of 1 to 2 nm, manufacturing may still be difficult, and the background tunneling current through the thin insulating layer may be too large to detect a signal from the nucleotide or such a thin insulating layer may not prevent shorting. Increasing the thickness of the insulating layer may allow for easier manufacturing, but then a measurable tunneling current would need to pass through even more nucleotides. A signal passing through multiple nucleotides would involve more complicated signal analysis to identify the individual nucleotides.

Embodiments of the present technology can reduce the noise in a current signal and do not require a thin insulating layer on the order of 1 to 2 nm. The tunneling junction devices may focus on reading a single nucleotide at a time. A single-stranded nucleic acid molecule (i.e., a template parent strand) may be attached or tethered to a tunneling junction. A double-stranded DNA molecule may be synthesized by polymerase connected to the template parent strand. Multiple template parent strands with multiple polymerases may be attached to the tunneling junction. Embodiments may include many tunneling junctions on the same device, allowing high multiplexing.

In some embodiments, a set of nucleotides of a single type (e.g., A nucleotides) are labeled with a moiety and introduced to the device. These nucleotides may be added to a nascent strand when the nucleotides are of a type complementary to the template parent strand. The device may be washed of excess free nucleotides at this time or later in a cycle after introducing additional labeled nucleotides.

An electric field may be applied to move the negatively charged nucleic acid molecule along with the moiety toward the tunneling junction (e.g., the insulating layer). The moiety may be brought close enough to allow current to tunnel from one conductor to the other conductor. In some embodiments, the moiety may contact both conductors to allow for a direct current path from one conductor to the other conductor. In embodiments where the moiety contacts both conductors to allow for a direct current path, the junction may be called a tunneling junction because the configuration of the junction may be similar or the same as a tunneling junction even though tunneling current is not the dominant current flowing through the junction. Multiple nucleic acid molecules attached to the tunneling junction may increase the probability of a current signal or may increase the strength of a current signal.

If the nucleotide is added to the DNA molecule, then the moiety causes a current signal in the tunneling junction. If the nucleotide is not added to the DNA molecule, then the current may be near zero. The moiety may be removed. A next type of labeled nucleotide can be introduced to the device, and the process may be repeated, thereby allowing a detection of whether a particular nucleotide is incorporated at each position. The current signal generated through the moiety may be higher than a background current through the nucleotide itself, thereby providing a signal with less noise.

I. Using Random Telegraphic Noise (RTN)

A tunneling current through the nucleotide or nucleotides themselves may not generate a high enough current signal with a suitable signal-to-noise ratio. The nucleotide may be in contact with the conductors for a short duration and the differences in tunneling currents between different nucleotides or sequences of nucleotides may be small. Accordingly, stronger and more easily detectable signals are desired.

A. RTN

To generate a current signal with a suitable signal-to-noise ratio, the current signal of embodiments of the present invention may mimic Random Telegraphic Noise (RTN), which previously referred to a problem with unwanted current signals in tunneling junctions. Without intending to be bound by a particular theory, one explanation for RTN is that impurities cause the unwanted current signals. The impurities may have trapped a charge and may sustain a higher current for a significant duration. The impurities may be imperfections in the oxide of the tunneling junction that act like charge traps. These impurities may include oxygen vacancies in the oxide, ions trapped in the metal oxide matrix, and substitute ions (e.g., dopants). After the impurity is no longer trapped the charge or the impurity left, the current drops. The devices in embodiments of the present invention intentionally recreate this RTN phenomenon with the tag of the labeled nucleotide.

FIG. 1 shows a graph 100 of RTN in a plot of current versus time. The graph shows areas of higher current (e.g., area 102) and areas of lower, near-zero current (e.g., area 104). The areas of higher current may have a trapped charge, while the areas of lower current may not have a trapped charge. The analysis of whether a charge may be trapped may then depend on identifying where a higher current than the background current is present.

B. Usage of Moiety

To intentionally mimic RTN, a moiety that generates RTN can be attached to the molecule of interest. For example, if the molecule to be analyzed is a nucleic acid, a moiety can be attached to a nucleotide to be incorporated into a growing nucleic acid strand.

Figure 2B:
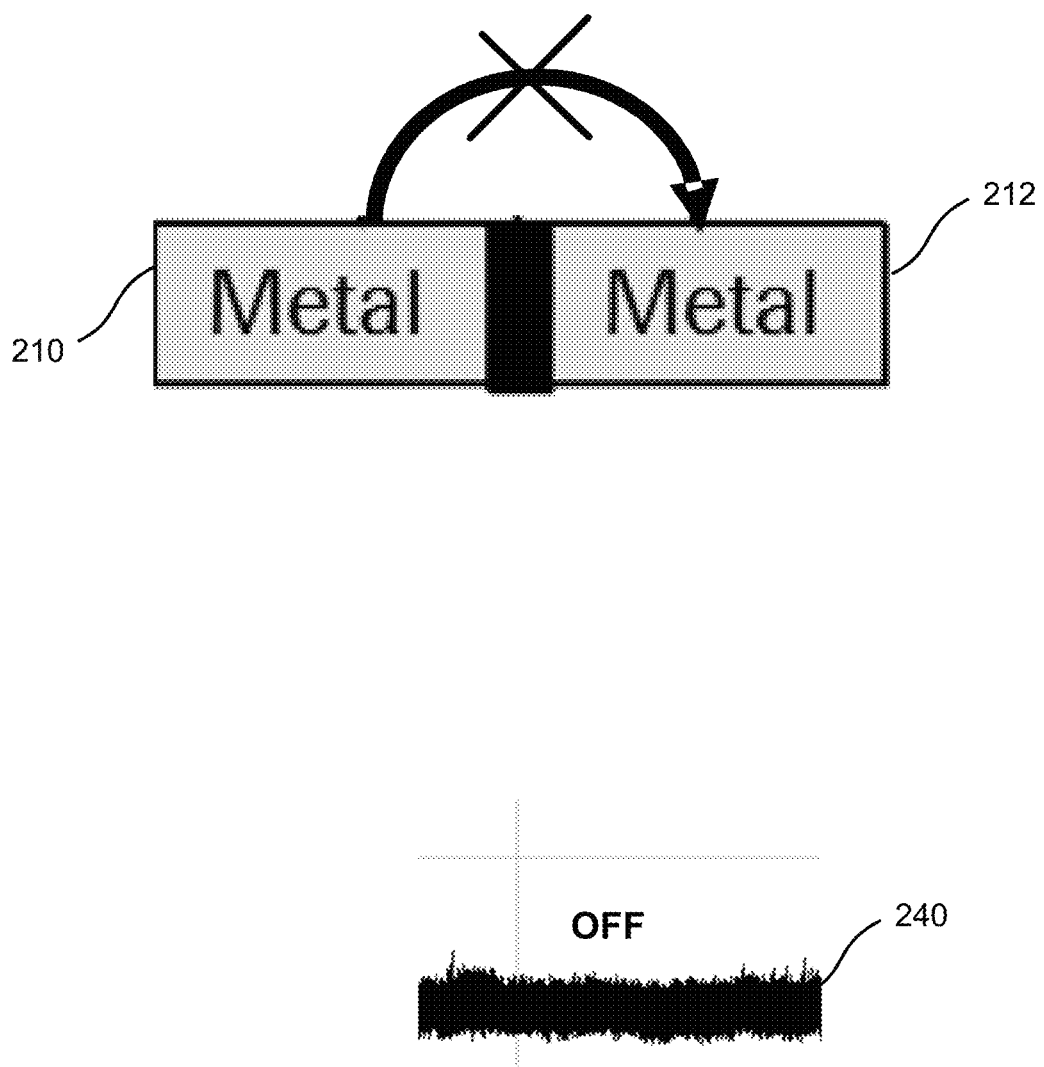

FIGS. 2A and 2B show how a moiety may be used to generate a current signal. In FIG. 2A, the last nucleotide added to a nascent strand 202 by a polymerase 204 is connected to a moiety 208. Nascent strand 202 is being hybridized to a template parent strand 206 by polymerase 204. If moiety 208 is sufficiently close to a first conductor 210 and a second conductor 212, moiety 208 allows for an electron to tunnel from first conductor 210 to second conductor 212. Tunneling electrons may generate a current signal versus time similar to graph 220. The random nature of the current signal may be a result of capture and release of the trapped charge state and/or capacitive effects (i.e., charge and discharge). The capacitive effects may result from a trapped electron changing the charge distribution around the tunneling junction, which may change the height of the tunneling barrier. The amplitude of the current flowing through the junction may depend exponentially on the barrier height. Small changes in the barrier height caused by random charging and discharging of the trap state may result in large changes in the tunneling current, which are evident in FIG. 2A.

In FIG. 2B, when no moiety is present, an electron cannot tunnel from first conductor 210 to second conductor 212. In FIG. 2B, the tunneling current should be near zero or near the background tunneling current, similar to graph 240. Hence, moiety 208 and therefore a nucleotide may be detected by measuring a tunneling current greater than zero or the background tunneling current.

The moiety should be an entity that allows the tunneling current to pass through based on a certain potential applied. FIG. 3A shows the tunneling current response when no moiety is attached to a nucleotide. A polymerase 302 is close to tunneling junction 304. Polymerase 302 is hybridizing template parent strand 306. No moiety is present, and no charge is trapped. The tunneling junction is in an off-resonance trap state 308, which does not allow current to tunnel from one conductor to the other conductor. The result is a graph 310 of current versus time where the current is near zero and at a background level.

FIG. 3B shows the tunneling current response when a moiety is attached to a nucleotide. A polymerase 312 is close to a tunneling junction 314. Polymerase 312 is hybridizing template parent strand 316. The nucleotide added has a moiety 318. Moiety 318 traps a charge at the electron transfer frequency. The tunneling junction is in an on-resonance trap state 320. A current can tunnel from one conductor through the moiety to the other conductor. The result is a graph 322 of current versus time where the current reaches a non-zero current and a current above a background level.

II. Label Compound with Moiety

The moiety used may be part of a label compound including more components than solely the moiety. The chemical compound used in methods and systems described herein may include a nucleotide, a cleavable linker, and a moiety. The nucleotide may include any of the four DNA nucleotides including adenine (A), thymine (T), guanine (G), and cytosine (C). The nucleotide may also include the four RNA nucleotides, including adenine, uracil (U), guanine, and cytosine. The label compound may be sufficiently long to allow contact of the moiety with the tunneling junction while an electrical field is applied to force the nucleic acid molecule at the moiety closer to the tunneling junction.

For electrical tunneling junctions, the moiety may be selected from the group consisting of an organometallic group, a nanoparticle, a conjugated aromatic group, and a conductive organic molecule. Conductive organic molecules may have no bandgaps and may not be insulators or semiconductors. As examples, organometallic groups may include ferrocene, metal phthalocyanines (e.g., manganese phthalocyanine), ruthenium, osmium, and transition metal organometallic compounds. As examples, nanoparticles may include gold, silver, platinum, magnesium, or titanium nitride nanoparticles. Nanoparticles may include any particles having a characteristic size from 1 to 10 nm, including from 1 to 5 nm and from 5 to 10 nm. The characteristic size may be the diameter of the nanoparticle if the nanoparticle is a sphere. However, if the nanoparticle is not a sphere, the characteristic size may be the diameter of a sphere having the same volume as the non-spherical nanoparticle. In some instances, the characteristic size may be the minimum of the width, length, or height of a nanoparticle. Conjugated aromatic groups may include a compound with several benzene rings, including a compound with two to nine benzene rings, anthracene, phenanthrene, tetracene, chrysene, triphenylene, pyrene, pentacene, benzopyrene, corannulene, benzoperylene, coronene, ovalene, and benzofluorene. The conjugated aromatic group may include a compound with benzene rings arranged in linear structure. As examples, conductive organic molecules may include short polymers including poly-pyrrole and poly-aniline.

The moiety, as mentioned above, may allow for a tunneling current by holding a charge in an on-resonance trap state. In some embodiments, the same moiety may be attached to the four nucleotides. In other embodiments, different moieties may be used for different nucleotides, with each moiety generating a different tunneling current for an applied voltage. The moiety may comprise multiple groups, such as multiple organometallic groups. The moiety may not be highly negatively or positively charged. A charged moiety may result in unwanted repulsion or attraction toward a DNA molecule.

For magnetic tunneling junctions, the moiety may be selected from the group consisting of a ferromagnetic or superparamagnetic material. Materials may include a magnetic nanoparticle (e.g., FePt, FeCuPt, $Fe_2O_3$). A nanoparticle may have a diameter or characteristic size less than 1 μm, 500 nm, 100 nm, or 10 nm.

The chemical compound may have a structure represented by N—X—S-M, where N is the nucleotide, X is the cleavable linker, S is a spacer, and M is the moiety. The nucleotide may be bonded directed to the cleavable linker.

The cleavable linker may allow the label compound to be cleaved from the incorporated nucleotide after detection. Cleavable linkers are known in the art and have been described e.g., in U.S. Pat. Nos. 7,057,026, 7,414,116 and continuations and improvements thereof. In some embodiments, the label is attached to the 5-position in pyrimidines or the 7-position in purines via a linker comprising an allyl or azido group. In other embodiments, the linker comprises a disulfide, indole or a Sieber group. The linker may further contain one or more substituents selected from alkyl ($C_{1-6}$) or alkoxy ($C_{1-6}$), nitro, cyano, fluoro groups or groups with similar properties. Briefly, the linker can be cleaved by water-soluble phosphines or phosphine-based transition metal-containing catalysts. Other linkers and linker cleavage mechanisms are known in the art. For example, linkers comprising trityl, p-alkoxybenzyl esters and p-alkoxybenzyl amides and tert-butyloxycarbonyl (Boc) groups and the acetal system can be cleaved under acidic conditions by a proton-releasing cleavage agent. A thioacetal or other sulfur-containing linker can be cleaved using a thiophilic metals, such as nickel, silver or mercury. Cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising O-nitrobenzyl groups. Linkers comprising benzyloxycarbonyl groups can be cleaved by Pd-based catalysts.

As examples, the cleavable linker X may be cleavable by a metal catalyst (e.g., an allyl group), an enzyme (e.g., protease cleavage site, Tobacco Etch Virus [TEV] cleavage site), light (e.g., nitrobenzene), reduction (e.g., disulfide), an acid (e.g., acetals, methoxymethyl, or protected acetals [e.g., O—$CH_2$—$N_3$ or —O—$CH(N_3)$—]), a base (e.g., succinate, acetyl), oxidation (e.g., vicinal diols), or a phosphatase (e.g., phosphate). The cleavable linker may include —O—$NH_2$, which may be cleaved with nitrite.

As examples, the spacer may be a polyethylene glycol (PEG), alkyl or aryl spacer, peptide, cationic spacer (e.g., spermine), nucleic acid, carbohydrate, or combinations thereof.

Figure 4A:
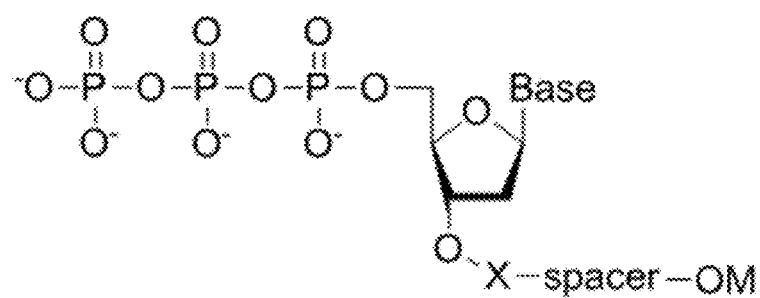
FIGS. 4A, 4B, and 4C show examples of a chemical compound that are modified nucleotides labeled with an organometallic moiety (OM) according to embodiments of the present invention.

FIG. 4A shows an example of a chemical compound. In FIG. 4A, the linker-spacer-moiety is attached to the 3' OH group of the deoxyribose sugar. The nucleotide is linked to X, the cleavable linker, a spacer, and then a organometallic (OM) moiety. Blocking the 3'-OH group may automatically terminate the polymerase reaction. However, a 3'-OH with a bulky compound may not be readily accepted by polymerases.

Figure 4B:
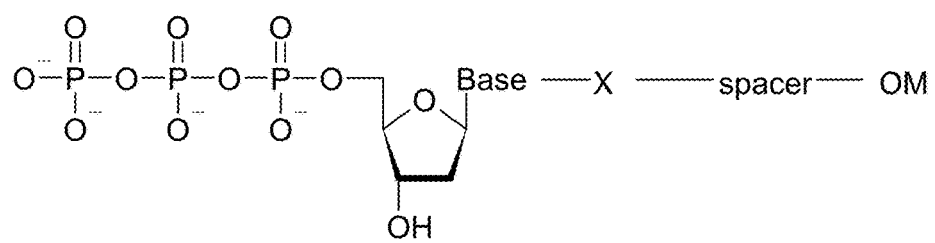

FIG. 4B shows an example of another chemical compound. The linker-spacer-moiety is attached to the base of the nucleotide. Modifying the base is usually well accepted by polymerases. However, because the 3'-OH group is not blocked, the compound in FIG. 4B may lead to less than 100% termination.

Figure 4C:
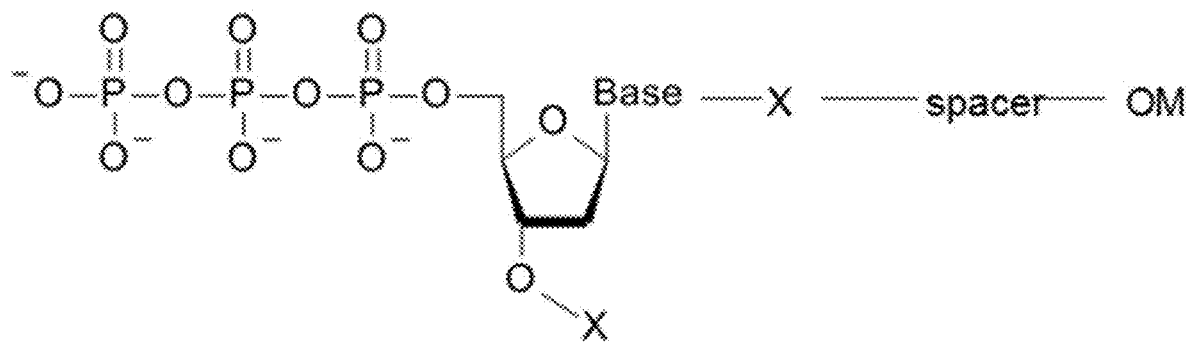

FIG. 4C shows yet another example of a chemical compound. Both the base and the 3' OH group can be bonded to a cleavable linker X. The linker X bonded to the base may be the same linker as X bonded to the 3' OH group. However, in some embodiments, the two linkers may be different compounds. The compound in FIG. 4C may incorporate the advantages of both the compound in FIG. 4A and the compound in FIG. 4B. Adding a small cleavable terminator group at the 3'-OH group may ensure a stop after incorporation. Attaching a large X—S-M compound onto the base may not disturb the polymerase too much. However, FIG. 4C may need to be cleaved at two sites instead of just one site.

The linker-spacer-moiety may act as a lightning terminator (Stupi, B. P. et al., "Stereochemistry of benzylic carbon substitution coupled with ring modification of 2-nitrobenzyl groups as key determinants for fast-cleaving reversible terminators," *Angew. Chem. Int. Ed.*, 51, 1724-1727 (2012), available at onlinelibrary.wiley.com/doi/epdf/10.1002/anie.201106516) or as a virtual terminator (Bowers, J. et al., "Virtual terminator nucleotides for next-generation DNA sequencing," *Nature Methods*, 6, 593-595 (2009), available at www.nature.com/articles/nmeth.1354. pdf and associated supplemental information available at media.nature.com/original/nature-assets/nmeth/journal/v6/n8/extref/nmeth.1354-S1. pdf).

The chemical compound may also include a terminator. The terminator may stop a polymerization process. For example, with a polymerase, the terminator may stop the polymerase from adding nucleotides until the terminator is removed. The linker, spacer, moiety, or the combination thereof may act as a terminator. The label compounds in FIGS. 4A, 4B, and 4C may each include a terminator.

If the molecule to be analyzed is not a nucleic acid, the chemical compound may be adapted accordingly. The label compound may be attached to a single unit of a biological polymer. For example, if the chemical compound to be analyzed is a protein, the label compound may be attached to an amino acid instead of a nucleotide.

III. Methods of Analyzing Molecule

The sequencing device may include two conductors separated by an insulating layer. The configuration of conductors and the insulating layer may be the same as a parallel plate capacitor or a tunneling junction. The tunneling junction may be an electrical tunneling junction or a magnetic tunneling junction. These configurations of conductors may be used to determine a sequence of a nucleic acid. Methods may include connecting a polymerase to a template parent strand attached to the sequencing device. The sequencing device may include a first conductor and a second conductor separated by an insulating layer. Methods may include adding a set of nucleotides to the sequencing device. Each nucleotide of the set of nucleotides may be attached to a label compound. The label compound may include a moiety.

Methods may further include elongating a nascent strand using the polymerase connected to the template parent strand to be sequenced. Elongating may include the polymerase incorporating a first nucleotide of the set of nucleotides into the nascent strand via hybridization to the template parent strand.

Methods may include applying an electric potential to move the template parent strand and a first moiety of a first label compound attached to the first nucleotide closer to the insulating layer while the template parent strand is attached to the sequencing device. Methods may then include measuring a value of an electrical or magnetic characteristic through the first conductor, the first moiety, and the second conductor while applying the electric potential. Methods may include detecting the first nucleotide as being hybridized to the template parent strand using the value of the electrical or magnetic characteristic.

Methods for electrical tunneling junctions and magnetic tunneling junctions are described below.

A. Electrical Field-Assisted Junction Configurations

FIGS. 5A-5G illustrate configurations used in determining a nucleic acid sequence. The sequencing device in FIGS. 5A-5G is provided to facilitate explanation, but sequencing devices and methods are not limited to the depictions in these figures.

Figure 5A:
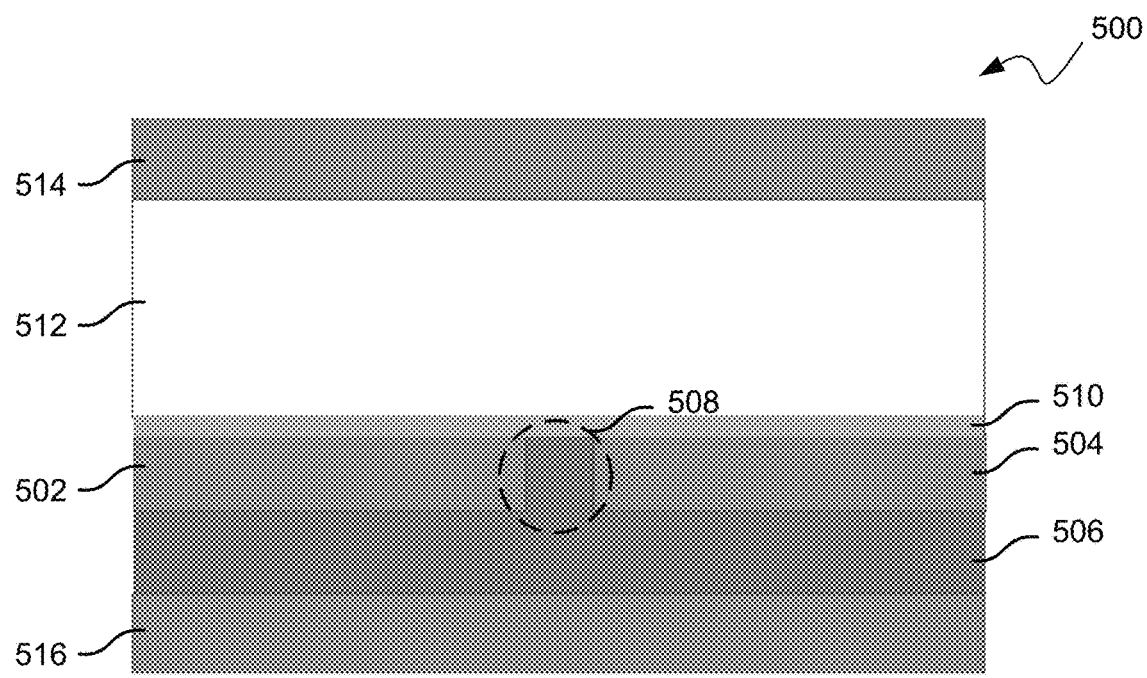

FIG. 5A shows a tunneling junction 500. Tunneling junction 500 includes a first tunneling electrode 502 and a second tunneling electrode 504. First tunneling electrode 502 and second tunneling electrode 504 are separated by an insulating material 506 that forms an insulating layer 508 between the two tunneling electrodes.

An adhesion layer 510 may be disposed on top of first tunneling electrode 502, second tunneling electrode 504, and insulating layer 508. Adhesion layer 510 may be a surface functionalization layer and may include silicon dioxide or alumina. The surface functionalization layer includes modifying a surface to include functional groups that allow for covalent bonding. First tunneling electrode 502 and second tunneling electrode 504 may be a metal material that does not allow for strong adhesion of nucleic acid molecules, and insulating layer 508 may be too thin for attaching nucleic acid molecules. Adhesion layer 510 allows for attachment of a nucleic acid molecule. The nucleic acid may attach to adhesion layer 510 by bonding with a compound that covalently bonds to silicon dioxide or alumina through an oxygen atom. The junction may be operational without adhesion layer 510.

A fluidic space 512 may separate adhesion layer 510 from a first field electrode 514. Fluidic space 512 may be filled with a liquid when tunneling junction 500 is being used for sequencing. In some embodiments, first field electrode 514 may not contact the liquid. For example, fluidic space 512 may be enclosed by a housing, which may be glass or plastic. First field electrode 514 may be outside the housing, but the electric field may still affect the space within the housing. Insulating material 506 may separate the tunneling electrodes from a second field electrode 516.

Figure 5B:
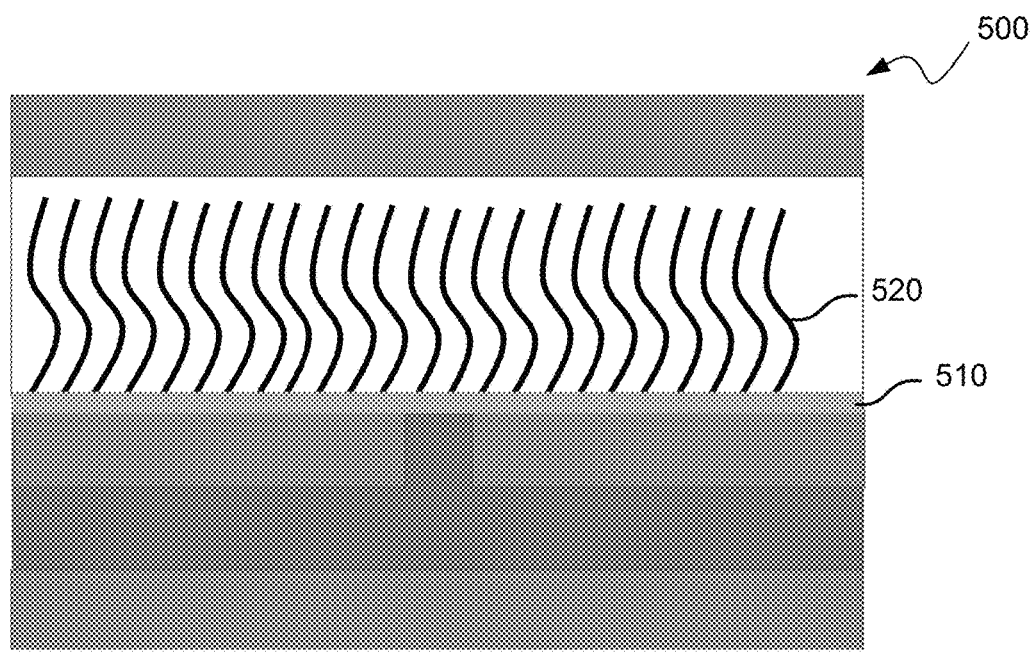

FIG. 5B shows tunneling junction 500 after identical copies of single-stranded DNA 520 are obtained. The identical copies of single-stranded DNA 520 may be obtained by bridge amplification. Bridge amplification may include adding adapters to both ends of DNA fragments. The adapters may include primers. These fragments may then be bound to a surface by an adapter. Both ends of a DNA fragment may be attached to the surface by the adapters forming a bridge-like structure. A polymerase synthesis the reverse strand of the DNA fragment to form a double-stranded DNA. The double-stranded DNA is then denatured to leave two strands of single-stranded DNA. The surface may be covered with a plurality of adapters. The adapters may be randomly distributed on the surface or arranged in a grid. There may be two types of adapters, with one type of adapter being complementary to an adapter at one end of the DNA fragment and a second type of adapter being complementary to an adapter at a second end of the DNA fragment. The two strands of single-stranded DNA may hybridize with the complementary adapter, forming two bridge-like structures. Each single-stranded DNA is hybridized to form double-stranded DNA. The double-stranded DNA is denatured again. The process may be repeated. As a result, the surface may be left with many single-stranded DNA densely attached to the surface. The identical copies may also be obtained by rolling circle amplification or other suitable amplification techniques. One type of adapter may be cleavable, and these adapters may be cleaved so that all the single-strands of DNA are attached to the surface at the same end (3' or 5'). Other techniques may be used to ensure all strands are in the same direction.

Single-stranded DNA 520 may be attached to adhesion layer 510. Single-stranded DNA 520 may attach to adhesion layer 510 more easily or more strongly than first tunneling electrode 502, second tunneling electrode 504, or insulating layer 508.

Figure 5C:
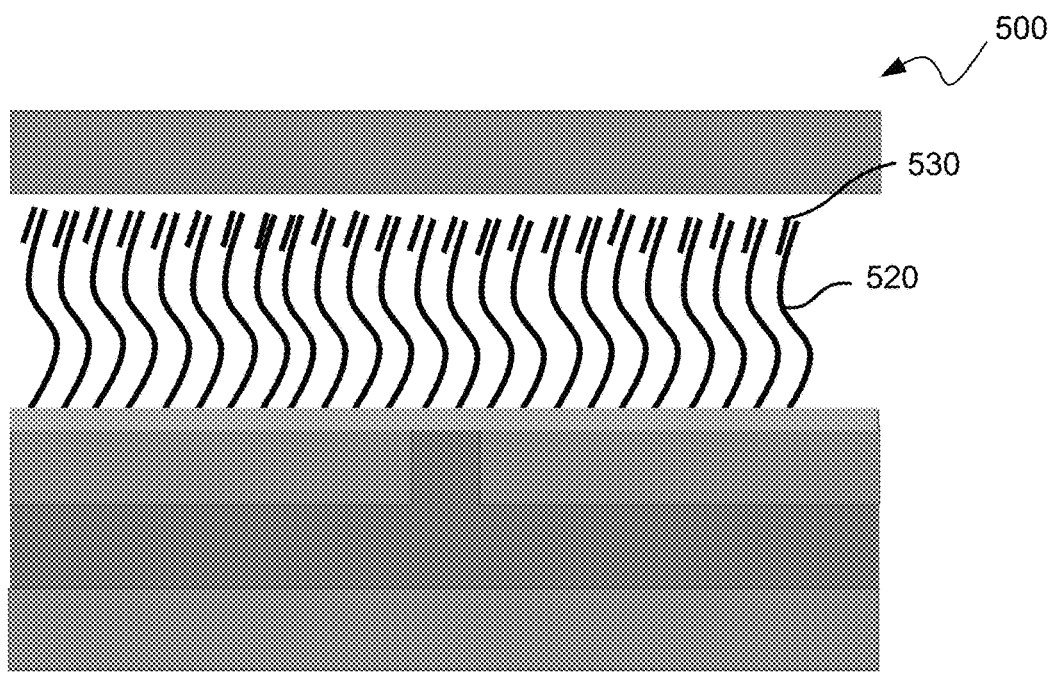

FIG. 5C shows tunneling junction 500 after adding primers. Primer 530 is added to single-stranded DNA 520 to form a section of double-stranded DNA. Each single-stranded DNA shown in FIG. 5C has a primer added to it.

Figure 5D:
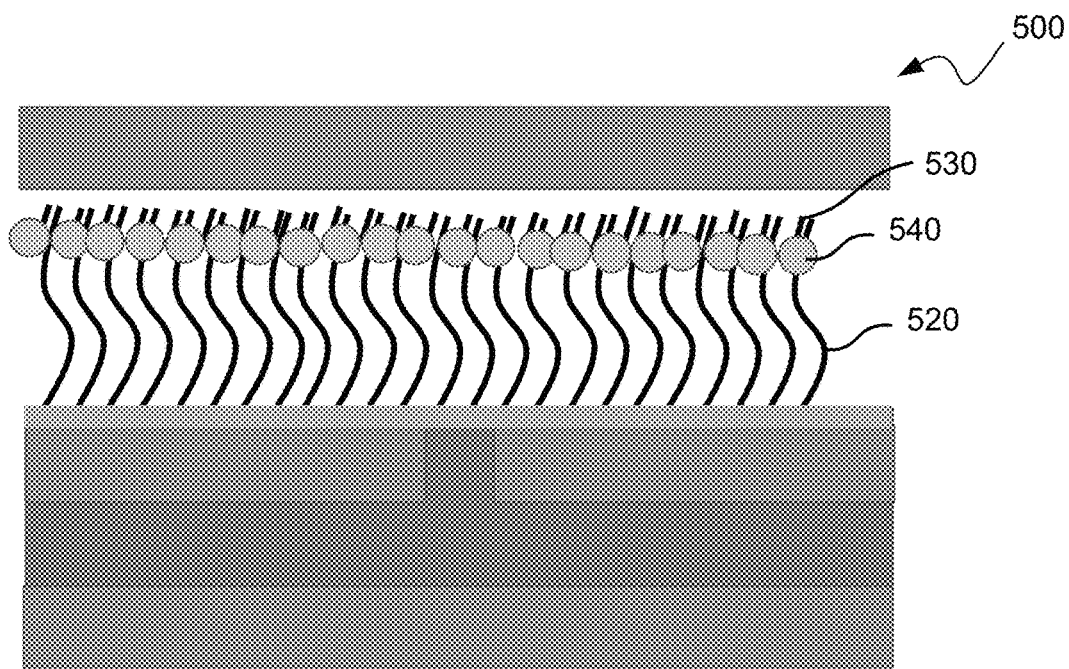

FIG. 5D shows tunneling junction 500 after adding polymerase. Polymerase 540 is connected to single-stranded DNA 520 and primer 530. Each single-stranded DNA shown in FIG. 5D has a polymerase connected to it.

Figure 5E:
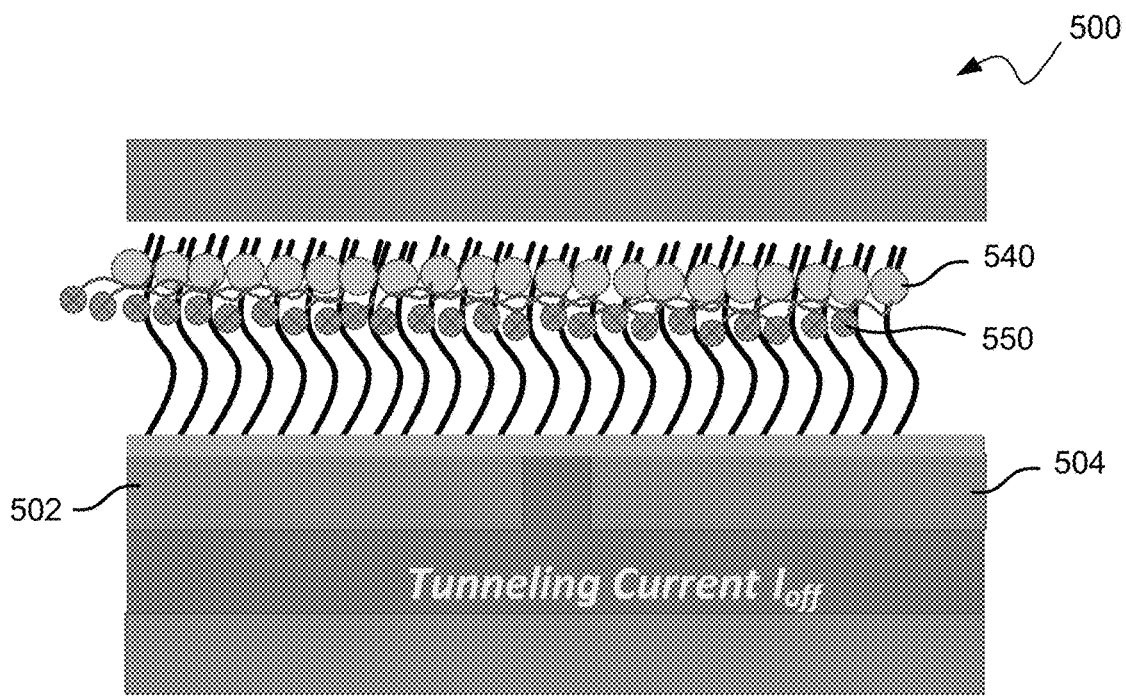

FIG. 5E shows tunneling junction 500 after a set of nucleotides is added. Nucleotides with label compounds are incorporated by the polymerase and hybridized to the single-stranded DNA. The nucleotides added may all be the same type of nucleotide. The label compounds may be any label compound described herein. As an example in FIG. 5E, polymerase 540 is incorporating a nucleotide with a label compound with moiety 550. The moieties are at a distance that do not significantly affect a tunneling current from first tunneling electrode 502 to second tunneling electrode 504.

Figure 5F:
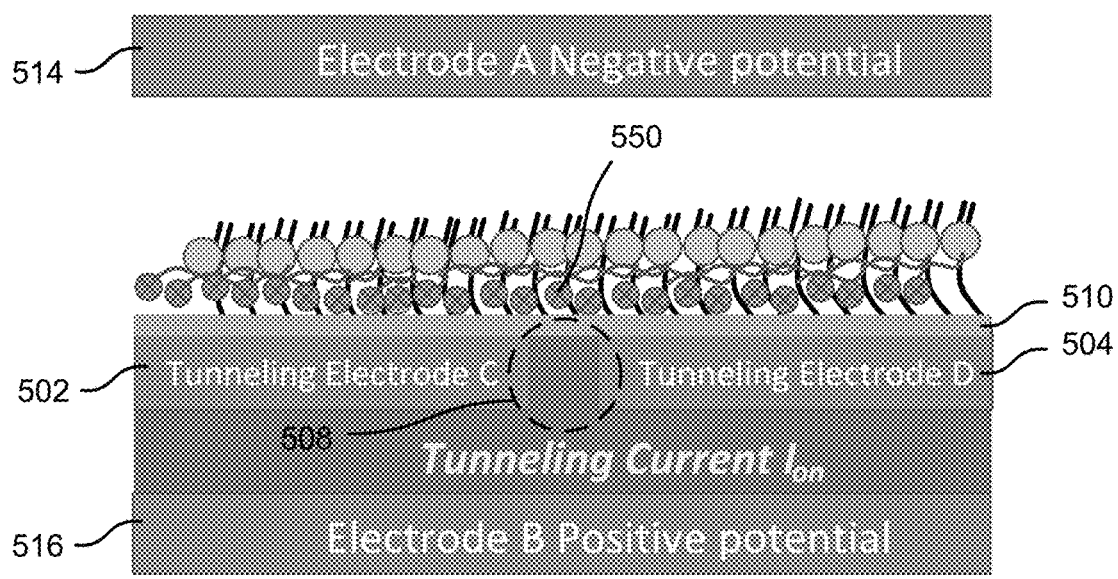

FIG. 5F shows detecting a nucleotide with tunneling junction 500. A negative potential is applied to first field electrode 514. A positive potential is applied to second field electrode 516. Because DNA is negatively charged, DNA moves away from first field electrode 514 and toward second field electrode 516. As a result, the DNA moves toward first tunneling electrode 502, insulating layer 508, and second tunneling electrode 504. Consequently, nucleotides with label compounds with moieties also move toward first tunneling electrode 502, insulating layer 508, and second tunneling electrode 504. For example, moiety 550 may move closer to first tunneling electrode 502, insulating layer 508, and second tunneling electrode 504. Moiety 550 may be at a distance where the tunneling current from first tunneling electrode 502 to second tunneling electrode 504 is affected by the presence of moiety 550 and a difference in tunneling current may be measured. Moieties near 550 connected to adjacent or nearby DNA may also affect the tunneling current similarly.

Although a negative voltage is described for first field electrode 514 and a positive voltage for second field electrode 516, one electrode need not be negative and the other electrode need not be positive. The electric field is based on the relative voltages between the two electrodes. For example, first field electrode 514 may have a positive voltage, and second field electrode 516 may have a positive voltage of an even greater magnitude.

The effect on tunneling current may result in the random telegraphic noise (RTN) described herein. In other words, the tunneling current may be higher when negative potential is applied to first field electrode 514 than when no negative potential is applied or when no nucleotide with a label compound including a moiety is incorporated. In some embodiments, a current may not undergo quantum tunneling but instead may travel from first tunneling electrode 502 to moiety 550 to second tunneling electrode 504.

Adhesion layer 510 is shown in FIG. 5F separating moiety 550 from first tunneling electrode 502, insulating layer 508, and second tunneling electrode 504. In some cases, additional polymerases may be added to replace some polymerases that may have detached from the DNA. FIG. 5F shows second field electrode 516 with a positive potential applied. However, second field electrode 516 need not be at a positive potential but instead should be positive with respect to first field electrode 514. Likewise, first field electrode 514 need not be at a negative potential but should be negative with respect to second field electrode 516. Additionally, both field electrodes may not be present as electrodes separate from the tunneling electrodes. For example, second field electrode 516 may not be present while first field electrode 514 is present. A negative potential is applied to first field electrode 514 relative to the potentials applied to first tunneling electrode 502 and/or second tunneling electrode 504. The tunneling electrodes may then act as the second field electrode. Similarly, second field electrode 516 may be present without first field electrode 514. A positive potential may be applied to second field electrode 516 relative to the fluid surrounding the DNA. The positive potential may attract DNA toward the tunneling junction.

Having adhesion layer 510 in this illustrated position would reduce the effect of moiety 550 on the tunneling current for a given distance. However, FIG. 5F is a two-dimensional rendering of tunneling junction 500 and does not exclude a configuration where adhesion layer 510 may not cover parts of first tunneling electrode 502, insulating layer 508, and/or second tunneling electrode 504.

FIG. 5G shows different possible top views of adhesion layer 510 where adhesion layer 510 may not cover parts of the underlying layers. In the top portion of FIG. 5G, adhesion layer 510 defines a circle that exposes a circular portion of insulating layer 508. The middle portion of FIG. 5G shows that adhesion layer 510 defines a rectangle, where a rectangular portion of insulating layer 508 is exposed. The bottom portion of FIG. 5G shows a configuration similar to the middle portion of FIG. 5G, except that portions of first tunneling electrode 502 and second tunneling electrode 504 are also exposed. Exposing the portions of first tunneling electrode 502 and second tunneling electrode 504 may allow for the electrodes to make direct contact with the moiety in order to obtain a signal.

Figure 5H:
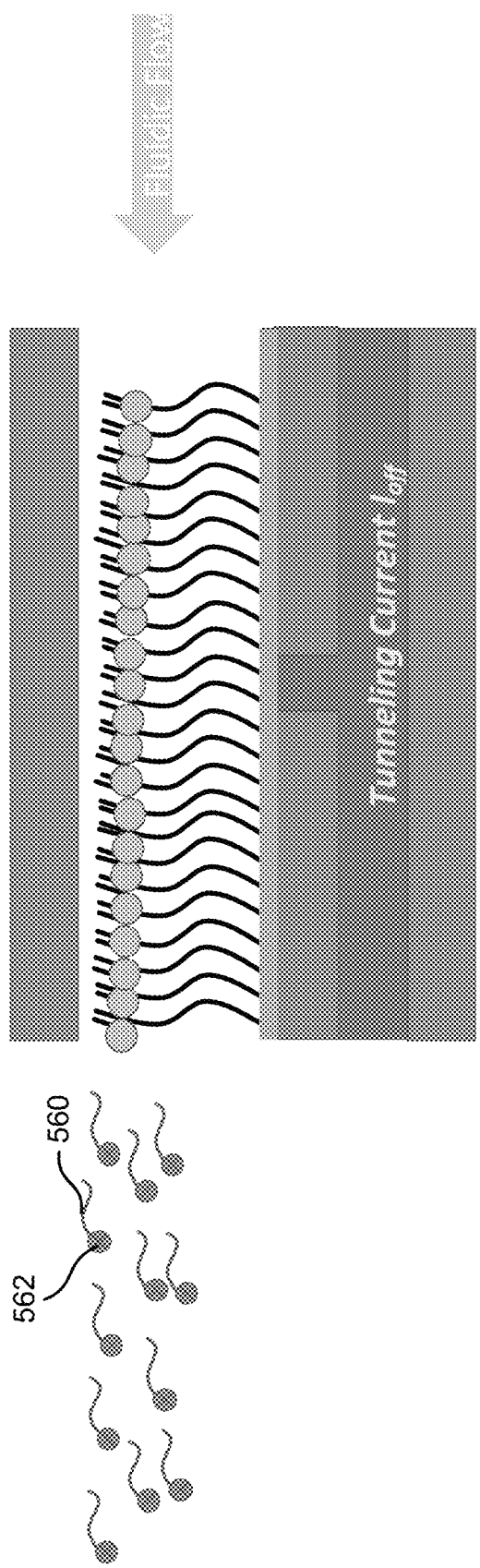

FIG. 5H shows tunneling junction 500 after removing label compounds from the nucleotide. The label compound includes a linker 560 and a moiety 562. The label compounds may be cleaved by photochemistry, chemistry, enzymatic reaction, or any technique described herein. The label compound may then be removed by flushing with a fluidic flow. If polymerases were removed, polymerases can be added again.

B. Example Method with Electrical Tunneling Junction.

FIG. 6 shows a method 600 of determining a sequence of a nucleic acid using a sequencing device according to embodiments of the present technology. The sequencing device may include an electrical tunneling junction, a first power supply, and a meter device. The tunneling junction includes a first conductor and a second conductor separated by an insulating layer. The first conductor and the second conductors may therefore be electrodes of the tunneling junction. The first power supply may be in electrical communication with the electrodes of the tunneling junction. A second power supply may be in electrical communication with a field electrode, which is separate from the electrodes of the tunneling junction.

Method 600 may include attaching a template parent strand to the sequencing device. Method 600 may further include attaching a primer to the template parent strand before block 602. In some embodiments, the template parent strand is one of a set of template parent strands. In these embodiments, a set of primers may be attached to the set of template parent strands. The device may resemble the illustration in FIG. 5C. In some embodiments, a second set of primers may be attached to the sequencing device, with the second set of primers being complementary to a first set of primers attached to the set of template parent strands. The template parent strands may then be attached to the sequencing device as a result of the first set of primers being attached to the second set of primers.

At block 602, a polymerase is connected to the template parent strand attached to the sequencing device. The template parent strand may be attached to an adhesion layer with primers attached to the adhesion layer, as explained above. The adhesion layer may contact the first conductor. In some embodiments, the adhesion layer may contact the second conductor and/or the insulating layer. The adhesion layer may include silicon dioxide, alumina, silicon, diamond-like carbon, silicon nitride, gold, or any suitable material that improves covalent bonding of the template parent strand to the tunneling junction.

In embodiments, the template parent strand may be one template parent strand of a set of template parent strands. The polymerase may be one polymerase of a set of polymerases. Methods may include connecting the set of polymerases to the set of template parent strands. Each polymerase of the set of polymerases may be connected to one and only one template parent strand of the set of template parent strands. Each template parent strand of the set of template parent strands may be connected to one and only one polymerase of the set of polymerases. After connecting the polymerase at block 602, the configuration may resemble the illustration of FIG. 5D.

The set of template parent strands may have been formed by amplifying a smaller set of template parent strands attached to the sequencing device. In some embodiments, the forward strands may be removed. In other embodiments the reverse strands may be removed. The remaining template parent strands may all be in the same direction and may be identical. Accordingly, the set of template parent strands can be formed by bridge amplification.

At block 604, a set of nucleotides is added to the sequencing device. Each nucleotide of the set of nucleotides is attached to a label compound including a moiety. The set of nucleotides may be added to the sequencing device by including the set of nucleotides in a liquid that contacts the sequencing device. The liquid may be an ionic liquid. The moiety may be selected from the group consisting of an organometallic compound, a nanoparticle, and a conjugated aromatic, or may be any moiety described herein. Each nucleotide of the set of nucleotides may be attached to a respective label compound including a respective moiety. In some embodiments, each nucleotide of the set of nucleotides may be the same type of nucleotide. For example, each nucleotide of the set of nucleotides may be G nucleotides. Each moiety of each label compound may be the same type of moiety. In other embodiments, the set of nucleotides may include two, three, or four types of nucleotides. In these embodiments, each nucleotide may be attached to a different type of moiety. The liquid with the set of nucleotides may be stored in a reservoir and introduced by an injection system to the tunneling junction.

At block 606, a nascent strand is elongated using the polymerase. The polymerase is connected to the template parent strand to be sequenced. Elongating includes the polymerase incorporating a first nucleotide of the set of nucleotides into the nascent strand. A nascent strand may be a single-stranded nucleic acid molecule. Elongating the strand may include incorporating a first nucleotide of the set of nucleotides into the nascent strand via hybridization to the template parent strand. Together, the nascent strand and the template parent strand may form a portion of a double-stranded nucleic acid molecule.

The label compound may include a terminator configured to prevent further elongation of the nascent strand. A problem with conventional tunneling junctions in sequencing may be that a molecule to be analyzed may flow past the junction too quickly, making contact with the electrode for a short duration. The current signal may then be too short and difficult to characterize. In addition, even if only one type of nucleotide is added in block 604, a particular sequence in the template parent strand may include the same type of nucleotide multiple times and consecutively. The nucleic acid molecule may then add multiple nucleotides of the same type from a single introduction. As a result, the device may generate only one signal for one nucleotide when multiple nucleotides have been added. The terminator may stop polymerase action until the terminator is removed. In this manner, only one nucleotide may be added at a time, allowing enough time for a current signal to be measured.

The set of nucleotides except the first nucleotide may be removed from contacting the tunneling junction. Removing the nucleotides may include rinsing the tunneling junction with water. The liquid used to rinse the tunneling junction may be water or an ionic liquid without a nucleotide. This rinse liquid may be stored in a reservoir and introduced to the tunneling junction with an injection system. Removing the set of nucleotides may occur before measuring a value of the electrical characteristic. In other embodiments, the set of nucleotides may not be removed before measuring the value of the electrical characteristic. After block 606, the device may resemble the configuration in FIG. 5E.

At block 608, an electric potential is applied to move the template parent strand and a first moiety of a first label compound attached to the first nucleotide closer to the insulating layer while the template parent strand is attached to the sequencing device. The electric potential may be applied by the second power supply mentioned above to the field electrode. In some embodiments, applying the electrical potential may move the first moiety of the first label compound to contact the first conductor and the second conductor. In embodiments, the first moiety may be moved to a distance where a current can tunnel from the first conductor through the first moiety to the second conductor when the voltage is applied across the first conductor and the second conductor.

Applying the electric field may include applying a negative voltage to an electrode. The negative voltage may be in a range from −1 V to 0 V, including −1 V to −0.75V, −0.75 V to −0.50 V, −0.50 V to −0.25 V, −0.25 V to −0 V. Applying the electrical field may include applying a positive voltage to another electrode. The positive voltage may be from 0 V to +1 V, including for example, 0 V to 0.25 V, 0.25 V to 0.50 V, 0.50 V to 0.75 V, or 0.75 V to 1.0 V. The voltage difference between the two electrode may be any voltage difference greater than 0 V and less than 2 V, including from 0.25 V to 0.50 V, from 0.50 V to 0.75 V, or 0.75 V to 1.0 V, from 1.0 V to 1.25 V, from 1.25 V to 1.50 V, from 1.50 V to 1.75 V, or from 1.75 V to 2.00 V. The electrode may be disposed such that the nascent strand is between the electrode and the insulating layer. The template parent strand, the polymerase, and/or the first label compound may be between the electrode and the insulating layer.

In some embodiments, strands that did not incorporate a nucleotide may be capped. Capping of strands allows for avoiding analyzing strands that have not incorporated any nucleotide after a cycle of nucleotides. For example, strands may not incorporate any of A, T, G, and C nucleotides after each one is introduced. If these strands then incorporate a nucleotide after the cycle, the strands would be out-of-phase with other strands that did incorporate a nucleotide within the last cycle. To reduce these out-of-phase readings, the strands may be capped so that they do not incorporate additional nucleotides.

At block 610, a voltage is applied across the first conductor and the second conductor. The voltage may be any voltage suitable to generate a current through an entity that contacts the tunneling junction. The current may be a tunneling current. The voltage may be applied after removing the set of nucleotides except for the first nucleotide (e.g., after rinsing). In some embodiments, the voltage may be applied for a longer duration, including before the rinse, during elongation (e.g., block 606), or during addition of the set of nucleotides (block 604). In some embodiments, a constant voltage may be applied throughout the method. The device may resemble the configuration in FIG. 5F.

At block 612, a value of an electrical characteristic through the first conductor, the first moiety, and the second conductor is measured. In embodiments, the first moiety may contact the first conductor and the second conductor. The electrical characteristic may be current, voltage, resistance, inductance, or pulse width. The value may be an average (mean, median, mode, root mean squared), a local or global maximum, or an instantaneous measurement. The value may be greater than 10 nA, greater than 100 nA, or greater than 1 μA.

At block 614, the first nucleotide is detected as being hybridized to the template parent strand using the value of the electrical characteristic. Blocks 616 and 618 describe how the first nucleotide may be detected.

At block 616, the value of the electrical characteristic may be compared to a reference value of the electrical characteristic. The reference value may be of a background tunneling current that is through the first electrode and the second electrode and that does not pass through the moiety. The reference value may be based on a background tunneling current. For example, the reference value may be set at a maximum level of the background tunneling current or set at a value that would be statistically different from a background electrical characteristic. For example, the reference value may be set at one, two, or three standard deviations from an average background tunneling current. In some embodiments, the reference value may be zero.

At block 618, the value may be determined to exceed the reference value. For example, the value may be determined to be greater than the background tunneling current. The current signal may be transformed into a binary signal of 1 when the value is determined to exceed the reference value.

1. Repeated Measurements with Another Nucleotide

Method 600 may further include repeating measurement and detection with another nucleotide after cleaving the first label compound. The first label compound may be cleaved, and a fluidic flow may remove the first label compound so that the device resembles that in FIG. 5H. Cleaving the first label compound removes a terminator, which allows the polymerase to elongate the nascent strand with additional nucleotides. Cleaving the first label compound may with photocleavage, which may include flashing a light at a certain wavelength or range of wavelengths to affect a photosensitive portion of the first label compound. In some embodiments, cleaving the first label compound may include chemically cleaving by introducing a cleaving agent, which may include a pH-adjusting agent (e.g., an acid or base), an enzyme, or a chemical reagent. In some embodiments, cleaving may be metal (e.g., palladium) catalyzed, reductive, oxidative, nucleophilic, or electrophilic.

Method 600 may include a second set of nucleotides being added the sequencing device. Each nucleotide of the second set of nucleotides is attached to a second label compound including a second moiety. Each nucleotide of the second set of nucleotides being a different type of nucleotide than the first nucleotide. Each second label compound may be the same as the first label compound. Each second moiety may be the same type of moiety as the first moiety.

After the nascent strand is elongated by incorporating the first nucleotide, the nascent strand may become an elongated nascent strand (i.e., the nascent strand with the addition of the first nucleotide). Method 600 may include further elongating the elongated nascent strand by the polymerase. The acid polymerase may incorporate a second nucleotide of the second set of nucleotides attached to the second label compound, which includes the second moiety.

A second value of the electrical characteristic through the first electrode, the second moiety, and the second electrode may be measured. Based on the second value of the electrical characteristic, the second nucleotide may be detected as being hybridized to the template parent strand. The measurement and detection may be the same as any measurement and detection described for the first nucleotide. In embodiments where the polymerase does not incorporate the second nucleotide or any nucleotide of the second set of nucleotides, the second value of the electrical characteristic may be determined as statistically equivalent to the reference value, and the absence of an additional nucleotide would be determined.

2. Multiple Types of Nucleotides in the Set of Nucleotides

In some embodiments, the set of nucleotides added in block 604 may include two or more types of nucleotides. The set of nucleotides may include a second nucleotide attached to a second label compound including a second moiety. Detecting the first nucleotide as being hybridized in block 610 may include comparing the value of the electrical characteristic in block 612. In method 600, the second nucleotide may be determined as not being hybridized to the template strand based on the value of the electrical characteristic by comparing the value of the electrical characteristic to a second reference value of the electrical characteristic. The second reference value may have a same value or a different value than the first reference value.

The first moiety may generate a value of an electrical characteristic in a certain range or above or below a certain value. The second moiety may generate a value of an electrical characteristic in a different range or above or below a certain value. The measured value of the electrical characteristic may be compared to the different ranges or values to determine which moiety, and therefore which nucleotide, is indicated by the value of the electrical characteristic. The first reference value and the second reference value may be an endpoint in ranges of values for the first moiety or the second moiety.

3. Multiple Tunneling Junctions

Method 600 may include determining a sequence of a nucleic acid using a plurality of tunneling junctions. Each tunneling junction may include a respective first electrode, a respective second electrode, and a respective insulating layer. Each respective tunneling junction is attached to a respective polymerase.

Method 600 may include steps for each tunneling junction of the plurality of tunneling junctions. A respective voltage may be applied across the respective first electrode and the respective second electrode. A respective nascent strand may be elongated using the respective polymerase attached to the respective tunneling junction and connected to a respective parent strand to be sequenced. Elongating may include the respective polymerase incorporating the respective nucleotide of the set of nucleotides into the respective nascent strand via hybridization to the respective template parent strand. A respective value of the electrical characteristic may be measured through the respective first electrode, the respective moiety of a respective label compound attached to the respective nucleotide, and the respective second electrode. The respective nucleotide may be detected as being hybridized to the respective template parent strand using the respective value of the electrical characteristic.

Each tunneling junction of the plurality of tunneling junctions may determine the presence or absence of a nucleotide being hybridized to the template parent strand. The plurality of junctions may number in the thousands, millions, or billions in a single device, which may be about a square centimeter. Because the detection involves identifying a binary signal of a 0 or 1, the read times for the tunneling junctions may be similar to that in a flash drive. Based on a flash drive, the read time for the tunneling junctions can be 80 megabits/sec (i.e., about 80 million junctions per second) to 5 gigabits/sec (i.e., about 5 billion junctions per second) or even faster. With tens of billions of tunneling junctions, the read time of all the tunneling junctions may be on the order of seconds. The wash cycle for the tunneling junctions may be on the order of 100 µs, less than the read time.

In embodiments, the first set of nucleotides is removed before the second set of nucleotides is added. In other embodiments the first set of nucleotides may not be removed (e.g., by a rinsing step) before the second set of nucleotides is added. In this manner, the second nucleotide may be hybridized to parent template strands at certain tunneling junctions. The total number of tunneling junctions with a current signal would be from any parent strands that have either a nucleotide from the first set of nucleotides or a nucleotide from the second set of nucleotides. Because the addition of nucleotides is done sequentially, the junctions with a nucleotide from the second set of nucleotides can be deduced based on the signals that did not appear with addition of the first set of nucleotides. This process can be then repeated with the remaining nucleotides. The wash can then be done after the multiple sets of nucleotides are introduced.

In some embodiments, with a plurality of tunneling junctions, two different types of nucleotides may be introduced at a time instead of a single nucleotide. A measurement may be made to see which tunneling junctions have included any of the two different types of nucleotides with two different label compounds. A first type of the nucleotide is then removed with a nucleotide-specific removal process. For example, label compounds with the first type of nucleotide may be removed with a certain wavelength of light, while the label compounds with the second type of nucleotide may not be removed from the nascent strand. After the removal, another measurement is made to identify tunneling junctions with the second type of nucleotide. As a result of this technique, the tunneling junctions that incorporated the first type of nucleotide, and the tunneling junctions that incorporated the second type of nucleotide can be determined. This technique may also be used for more than two types of nucleotides, so long as the label compounds for the types of nucleotides can be selectively removed.

Method 600 may be adapted for analyzing molecules other than nucleic acid sequences. For example, if a protein is to be analyzed for the amino acid sequence, the polymerase may be replaced by a ribosome. The amino acid would be labeled instead of the nucleotide. Depending on the molecule to be analyzed, the polymerase may also be replaced by a helicase, an exonuclease, along with other enzymes.

C. Magnetic Tunneling Junction Configurations

Figure 7:
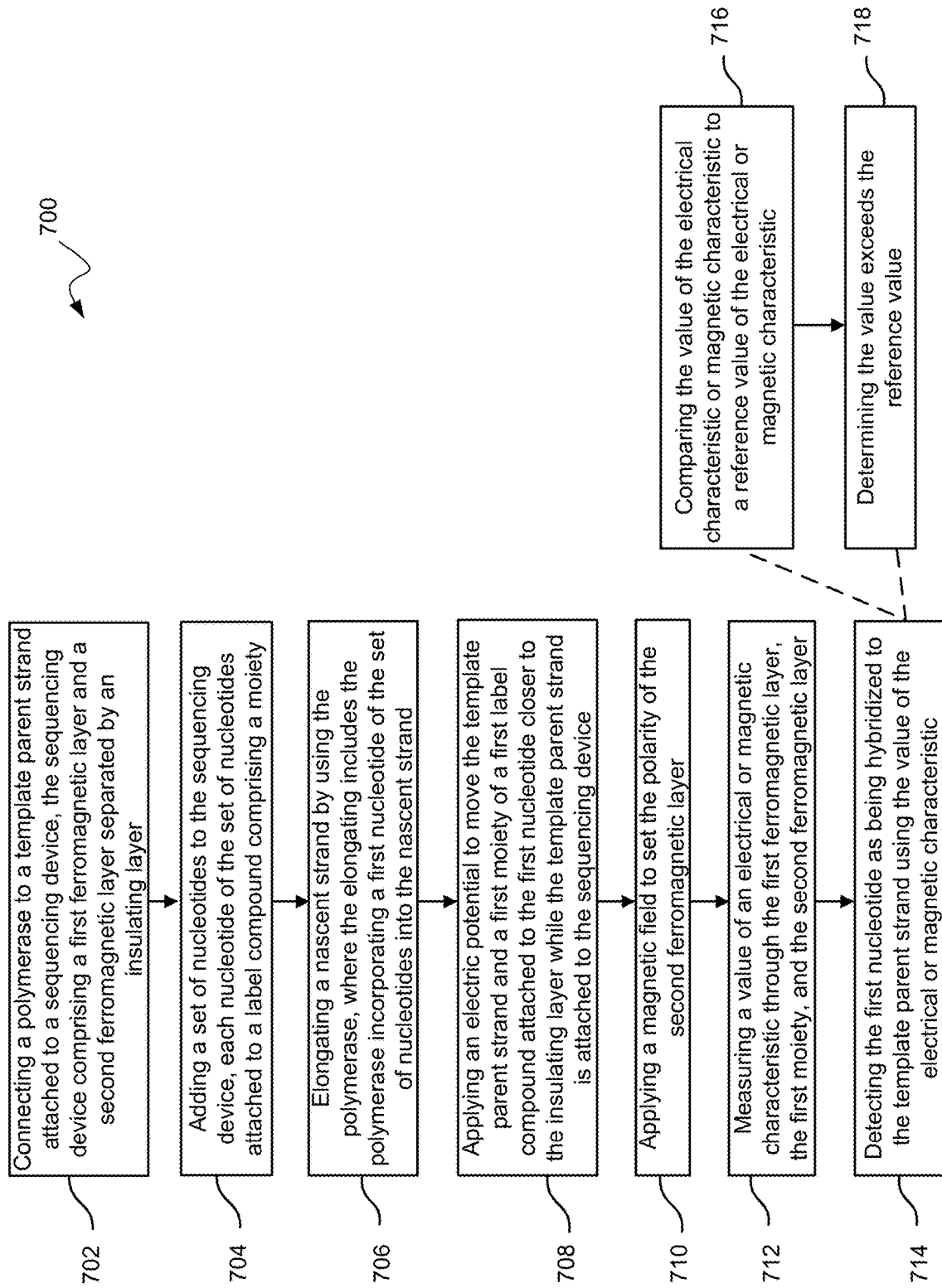
FIG. 7 illustrates steps of determining a nucleic acid sequence with a magnetic tunneling junction according to embodiments of the present invention.

FIG. 7 shows a method 700 of determining a sequence of a nucleic acid using a sequencing device according to embodiments of the present technology. The sequencing device may include a magnetic tunneling junction, a first power supply, and a meter device. The tunneling junction includes a first ferromagnetic layer and a second ferromagnetic layer separated by an insulating layer. The ferromagnetic layer and the second ferromagnetic layer are examples of conductors described for tunneling junctions. The first power supply may be in electrical communication with the conductors of the tunneling junction. A second power supply may be in electrical communication with a field electrode, which is separate from the conductors of the tunneling junction.

Method 700 may include introducing a template parent strand to the tunneling junction. The template parent strand may be introduced to the tunneling junction with a fluid injection system. The template parent strand may be obtained from a biological sample. The template parent strand may be attached to the tunneling junction in any manner described herein. The device may resemble the illustration in FIG. 5C.

At block 702, a polymerase is connected to a template parent strand attached to the sequencing device. The template parent strand may be attached to an adhesion layer in any manner described herein. The adhesion layer may contact the first ferromagnetic layer. In some embodiments, the adhesion layer may contact the second ferromagnetic layer and/or the insulating layer. The adhesion layer may include silicon dioxide or any suitable material that improves adhesion of the template parent strand to the tunneling junction. After connecting the polymerase at block 702, the configuration may resemble the illustration of FIG. 5D.

In embodiments, the template parent strand may be one template parent strand of a set of template parent strands. The set of template strands may have all be in the same direction (forward or reverse). The polymerase may be one polymerase of a set of polymerases. Methods may include connecting the set of polymerases to the set of template parent strands. Each polymerase of the set of polymerases may be connected to one and only one template parent strand of the set of template parent strands. Each template parent strand of the set of template parent strands may be connected to one and only one polymerase of the set of polymerases.

The set of template parent strands may have been formed by amplifying a smaller set of template parent strands attached to the sequencing device. The set of template parent strands may have been formed by bridge amplification.

At block 704, a set of nucleotides is added to the sequencing device. Each nucleotide of the set of nucleotides is attached to a label compound including a moiety. The set of nucleotides may be added to the sequencing device by including the set of nucleotides in a liquid that contacts the sequencing device. The liquid may be an ionic liquid. The moiety may be selected from the group consisting of a ferromagnetic or superparamagnetic material. The material may include a magnetic nanoparticle (e.g., FePt, FeCuPt, $Fe_2O_3$) or may be any moiety described herein. Each nucleotide of the set of nucleotides may be attached to a respective label compound including a respective moiety. In some embodiments, each nucleotide of the set of nucleotides may be the same type of nucleotide. For example, each nucleotide of the set of nucleotides may be G nucleotides. Each moiety of each label compound may be the same type of moiety. In other embodiments, the set of nucleotides may include two, three, or four types of nucleotides. In these embodiments, each nucleotide may be attached to a different type of moiety. The liquid with the set of nucleotides may be stored in a reservoir and introduced by an injection system to the tunneling junction.

At block 706, a nascent strand is elongated using the polymerase. Elongating includes the polymerase incorporating the first nucleotide of the set of nucleotides into the nascent strand. A nascent strand may be a single-stranded nucleic acid molecule. Elongating the strand may include incorporating a first nucleotide of the set of nucleotides into the nascent strand via hybridization to the template parent strand. Together, the nascent strand and the template parent strand may form a portion of a double-stranded nucleic acid molecule.

The label compound may include a terminator configured to prevent further elongation of the nascent strand. Similar to the label compound used with electrical tunneling junctions, the label compound used with magnetic tunneling junctions is configured to allow for a longer signal by including a terminator.

The set of nucleotides except the first nucleotide may be removed from contacting the tunneling junction. Removing the nucleotides may include rinsing the tunneling junction with water. The liquid used to rinse the tunneling junction may be water or an ionic liquid without a nucleotide. This rinse liquid may be stored in a reservoir and introduced to the tunneling junction with an injection system. Removing the set of nucleotides may occur before measuring a value of the electrical or magnetic characteristic. In other embodiments, the set of nucleotides may not be removed before measuring the value of the electrical or magnetic characteristic. After block 706, the device may resemble the configuration in FIG. 5E.

At block 708, an electric potential is applied to move the template parent strand and a first moiety of a first label compound attached to the first nucleotide closer to the insulating layer while the template parent strand is attached to the sequencing device. The electric potential may be applied by the second power supply mentioned above to the field electrode.

At block 710, a magnetic field may be applied to set the polarity of the second ferromagnetic layer. The first ferromagnetic layer may be a permanent magnet and may have a first polarity. The magnetic field may be applied to the second ferromagnetic layer to set the polarity at a second polarity that is antiparallel to the first polarity. The magnetic field may be applied by an external magnet. The magnetic field may be applied after removing the set of nucleotides except for the first nucleotide (e.g., after rinsing). In some embodiments, the voltage may be applied for a longer duration, including before the rinse, during elongation (e.g., block 706), or during addition of the set of nucleotides (block 704). In some embodiments, a constant magnetic field may be applied throughout the method. The device may resemble the configuration in FIG. 5F.

At block 712, a value of an electrical or magnetic characteristic through the first ferromagnetic layer, the first moiety, and the second ferromagnetic layer is measured. The electrical characteristic may be current, voltage, resistance, inductance, or pulse width. The value may be an average (mean, median, mode, root mean squared), a local or global maximum, or an instantaneous measurement. The value may be greater than 10 nA, greater than 100 nA, or greater than 1 µA. The magnetic characteristic may be a magnetic field perturbation caused by magnetic nanoparticles and measured by magnetic sensors.

At block 714, the first nucleotide may be detected as being hybridized to the template parent strand using the value of the electrical or magnetic characteristic. Blocks 716 and 718 describe how the first nucleotide may be detected.

At block 716, the value of the electrical or magnetic characteristic may be compared to a reference value of the electrical or magnetic characteristic. The reference value may be of a background tunneling current, resistance, or other electrical characteristic that is through the first ferromagnetic layer and the second ferromagnetic layer and that does not pass through the moiety. The reference value may be based on a background tunneling current. For example, the reference value may be set at a maximum level of the background tunneling current or set at a value that would be statistically different from a background electrical characteristic. For example, the reference value may be set at one, two, or three standard deviations from an average background tunneling current. In some embodiments, the reference value may be zero.

At block 718, the value may be determined to exceed the reference value. For example, the value may be determined to be greater than the background tunneling current. The current signal may be transformed into a binary signal of 1 when the value is determined to exceed the reference value.

Method 700 may include cleaving the first label compound from the first nucleotide. The first label compound may be cleaved, and a fluidic flow may remove the first label compound so that the device resembles that in FIG. 5H. Cleaving the first label compound removes a terminator, which allows the polymerase to elongate the nascent strand with additional nucleotides. Cleaving the first label compound may with photocleavage, which may include flashing a light at a certain wavelength or range of wavelengths to affect a photosensitive portion of the first label compound. In some embodiments, cleaving the first label compound may include chemically cleaving by introducing a cleaving agent, which may include a pH-adjusting agent (e.g., an acid or base), an enzyme, or a chemical reagent. In some embodiments, cleaving may be metal (e.g., palladium) catalyzed, reductive, oxidative, nucleophilic, or electrophilic.

Method 700 may include repeated measurements with another nucleotide, multiple types of nucleotides in the set of nucleotides, and/or multiple tunneling junctions similar to what has been described for electrical tunneling junctions. Similar to method 600, method 700 may be adapted for analyzing molecules other than nucleic acid sequences.

IV. Analysis System

Methods to determine the sequence of a nucleic acid may include using a system with a tunneling junction or capacitor-like structure. The system may include a sequencing device. The sequencing device may include a first conductor and a second conductor separated by an insulating layer. The conductors may be electrodes or ferromagnetic layers of a tunneling junction. The system may include an adhesion layer contacting at least one of the first conductor or the second conductor. A template parent strand may be attached to the sequencing device. In particular, the template parent strand may be attached to the adhesion layer. A first power supply may be in electrical communication with at least one of the first conductor or the second conductor.

An electrode, which is not a conductor of the tunneling junction, may be disposed such that the template parent strand is between the electrode and the insulating layer. A second power supply may be in electrical communication with the electrode. The second power supply may be configured to apply a voltage to the electrode. The system may include a set of nucleotides. Each nucleotide of the set of nucleotides may be attached to a label compound including a moiety. The system may further include a meter device configured to measure a value of a characteristic through the first conductor and the second conductor via the moiety. The characteristic may be an electrical characteristic or a magnetic characteristic.

The system may include a control system. The control system may be configured to apply the voltage using the second power supply while measuring the value of the characteristic using the meter device. The control system may include a computer with a computer readable medium storing a plurality of instructions. The plurality of instructions, when executed by a processor, may cause the processor to measure the value of the characteristic through the first conductor and the second conductor. The instructions may also cause the processor to compare the value of the characteristic to a reference value of the characteristic. Upon determining the value exceeds the reference value, the instructions may cause the processor to detect a nucleotide as being hybridized to the template parent strand. In some embodiments, the control system may include a field-programmable gate array (FPGA) or application-specific integrated circuit (ASIC). The FPGA or ASIC may be configured to perform operations described for the processor in a computer system. For example, the FPGA or ASIC may compare the value of the characteristic to a reference value of the characteristic. The FPGA or ASIC, upon determining the value exceeds the reference value, may detect a nucleotide as being hybridized to the template parent strand. The FPGA or ASIC may be on the same substrate as the sequencing device. In other words, the FPGA or ASIC may be on the same chip as the sequencing device. The control system may include any combination of a computer, an FPGA, and an ASIC, with operations divided among these components.

Systems related to electrical tunneling junctions and magnetic tunneling junctions are described below.

A. Electrical Tunneling Junction Systems

Figure 8A:
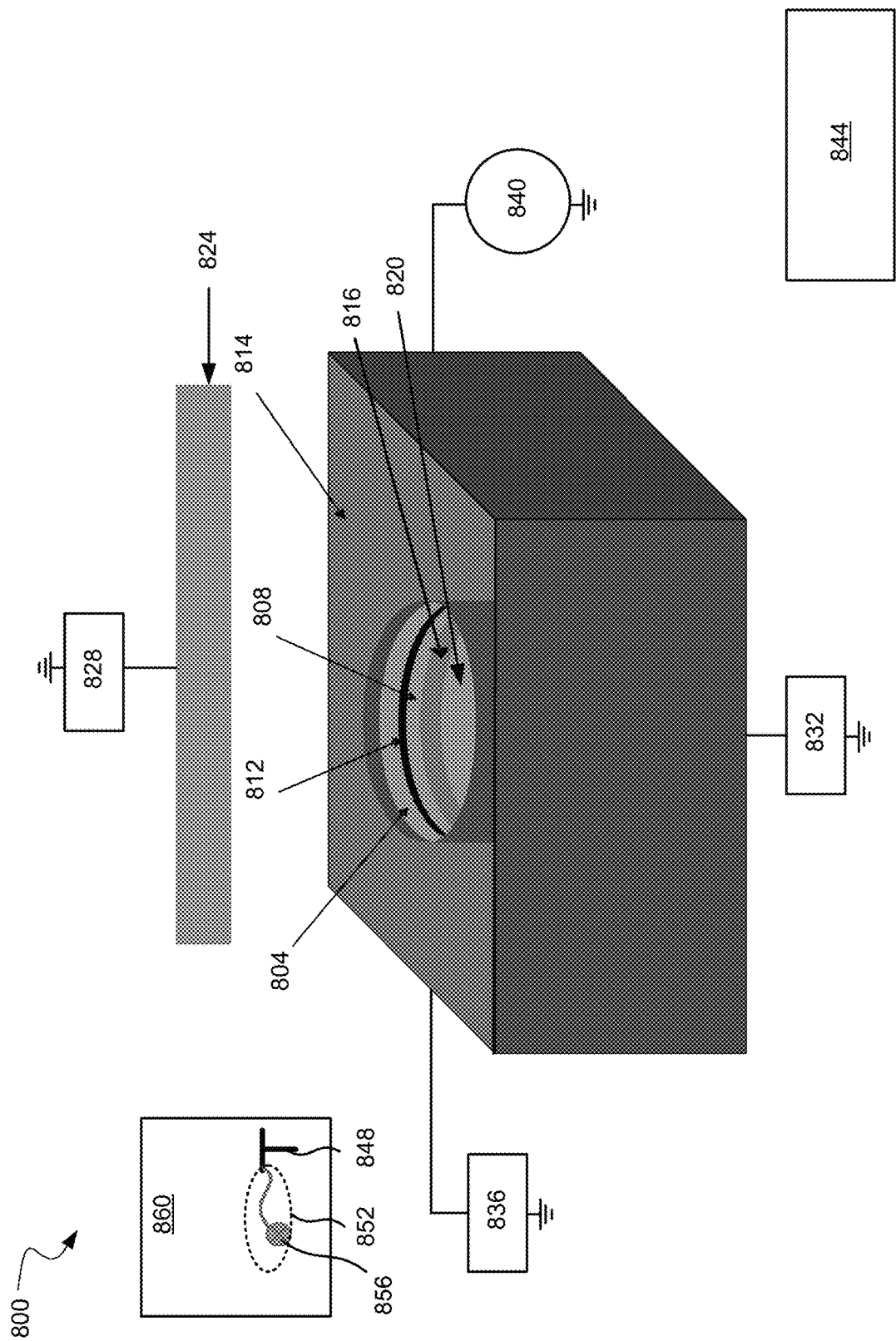
FIGS. 8A-8C shows an example system used in determining a nucleic acid sequence according to embodiments of the present invention.

FIG. 8A shows an example system 800. System 800 may include a tunneling junction. Tunneling junction includes a first electrode 804, a second electrode 808, and an insulating layer 812. The electrode materials may include gold, silver, platinum, or palladium. The electrode may include any metal that has a metal oxide that is chemically stable in the aqueous solution used as the medium for the molecule to be analyzed. Other metals may include tantalum, nickel, chrome, titanium, and copper.

Insulating layer 812 may include a dielectric material, including alumina ($Al_2O_3$), hafnia ($HfO_2$), silicon nitride ($Si_3N_4$), silicon oxide ($SiO_2$), glass, quartz, magnesium oxide (MgO), titanium dioxide ($TiO_2$), or zirconium dioxide ($ZrO_2$). Insulating layer 812 may have a thickness greater than 2 nm. The thickness may be the distance between first electrode 804 and second electrode 808. Because operation of the tunnel junction does not require the nucleotide or nucleotides of a nucleic acid molecule to contact both electrodes, the width of the insulating layer may be greater than the size of a nucleotide or nucleotides. In addition, the width of the insulating layer may be larger than the size of the moiety as tunneling may still occur even if the moiety is smaller than the gap between the electrodes.

Adhesion layer 814 may contact first electrode 804. Adhesion layer 814 allows for a stronger contact between the a surface and a nucleic acid molecule than the electrode material. Adhesion layer 814 may include silicon dioxide.

The tunneling junction may be a portion of an aperture or a pore that extends all the way through a substrate. First electrode 804, second electrode 808, insulating layer 812, and adhesion layer 814 may define an aperture or a portion of an aperture. In other embodiments, such as the tunneling junction shown in FIG. 8A, the tunneling junction is a portion of a trench, via, well, or other structure that does not extend all the way through a substrate. Second electrode 808 may contact an isolation layer 816. Isolation layer 816 may be an insulating material, including silicon dioxide. Isolation layer 816 may isolate or insulate second electrode 808 from first field electrode 820.

In some embodiments, the tunneling junction may not be an aperture or a via. Instead, the tunneling junction may be on the sidewall of a feature. The feature may be a trench, a cylinder, or a rectangular solid. The electrodes, the insulating layer, and the adhesion layer may define the sidewall or a portion of the sidewall of the feature.

First field electrode 820 may form the bottom of the tunneling junction. Second field electrode 824 may be positioned so that first electrode 804, second electrode 808, and insulating layer 812 are between first field electrode 820 and second field electrode 824. First field electrode 820 and second field electrode 824 may be any electrode material described herein. In addition, first field electrode 820 and second field electrode 824 may not be exposed to liquid and may therefore be made of any conducting or semiconducting material. However, second field electrode 824 may not be first electrode 804 and/or second electrode 808.

Second field electrode 824 may be in electrical communication with power supply 828. Power supply 828 may be configured to deliver a negative potential or voltage to second field electrode 824. First field electrode 820 may be in electrical communication with power supply 832. Power supply 832 may be configured to deliver a positive potential or voltage to first field electrode 820. Power supply 828 may apply a voltage to second field electrode 824 that is more negative than the voltage applied by power supply 832 to first field electrode 820. In some embodiments, power supply 832 is not present and first field electrode 820 is at or near ground potential. As explained previously, first field electrode 820 may not be an electrode separate from the tunneling electrodes (first electrode 804 and second electrode 808).

System 800 may include a power supply 836. Power supply 836 may be in electrical communication with at least one of first electrode 804 and second electrode 808. Power supply 836 may apply a voltage to first electrode 804 and second electrode 808. Power supply 836 may be configured to maintain a desired current or a desired voltage. Power supply 836 may provide voltages from 0 to 1 V, including from 10 mV to 100 mV, from 100 mV to 200 mV, from 200 mV to 300 mV, from 300 mV to 500 mV, or from 500 mV to 1 V. In some embodiments, power supply 836 may provide currents of 0 to 30 nA, including from 1 pA to 10 pA, from 10 pA to 100 pA, from 100 pA to 1 nA, 1 nA to 10 nA, or from 10 nA to 30 nA.

System 800 may also include a meter device 840. Meter device 840 may be configured to measure a value of an electrical characteristic through first electrode 804 and second electrode 808. Meter device 840 may be a current meter, a voltage meter, or an oscilloscope. The electrical characteristic may be current or voltage.

The electrical connections are simplified in FIG. 8A for illustrative simplicity and in many cases do not show the direct connection between devices and electrodes.

System 800 may include a control system 844. Control system 844 may be in communication with power supply 836 and meter device 840. In addition, control system 844 may be in communication with power supply 828 and power supply 832. Control system 844 may also be in communication with control systems that deliver fluid to the tunneling junction. Control system 844 may include a computer system with a processor and a computer readable medium. The computer readable medium may be store a plurality of instructions. The plurality of instructions, when executed by a processor, may cause the processor to perform any method described herein. For example, the plurality of instructions, when executed, may cause the processor to measure the value of the electrical characteristic through the first electrode and the second electrode. The processor may also be caused to compare the value of the electrical characteristic to a reference value of the electrical characteristic. Upon determining the value exceeds the reference value, the processor may further be caused to detect a nucleotide as being hybridized to the template parent strand. Upon determining the value does not exceed the reference value, the processor may further be caused to determine the absence of the nucleotide being hybridized to the template parent strand. Control system 844 may include an FPGA or an ASIC. The FPGA or the ASIC may be configured to perform any operation described above for execution by the processor of the computer system. The FPGA or the ASIC may be on the same chip as the tunneling junction. Control system 844 is described in greater detail below.

System 800 may include a nucleotide 848 attached to a label compound 852. Label compound 852 may include a moiety. Label compound 852 may be any label compound described herein. The moiety may be any moiety described herein.

System 800 may include a reservoir 860. Reservoir 860 may be in fluid communication with the tunneling junction. An injection system may be configured to deliver a liquid (e.g., including water) from reservoir 860 to the tunneling junction. Reservoir 860 may include nucleotide 848 attached to label compound 852. In some embodiments, system 800 may include a plurality of reservoirs. Each reservoir may include a different liquid to be injected to the tunneling junction. For example, a different reservoir may be used for each of the four types of nucleotide. An additional reservoir may be included to deliver water to rinse the nucleotides from the tunneling junction. Another reservoir may deliver a set of polymerases to the tunneling junction. Each polymerase of the set of polymerases may be configured to elongate a nascent nucleic acid molecule strand that is hybridized to the parent nucleic acid molecule strand.

System 800 may include a plurality of tunneling junctions. The plurality of tunneling junctions may number in the thousands, millions, or billions per square centimeter. Each tunneling junction may be on the surface of the same substrate. The substrate may include a semiconductor wafer, including a silicon wafer or silicon-on-insulator wafer. Each tunneling junction may be fabricated using semiconductor processing techniques. Each tunneling junction may be identical. Power supply 836 may be in electrical communication with the plurality of tunneling junctions. Meter device 840 or a plurality of meter devices may be in electrical communication with the plurality of tunneling junctions.

Figure 8B:
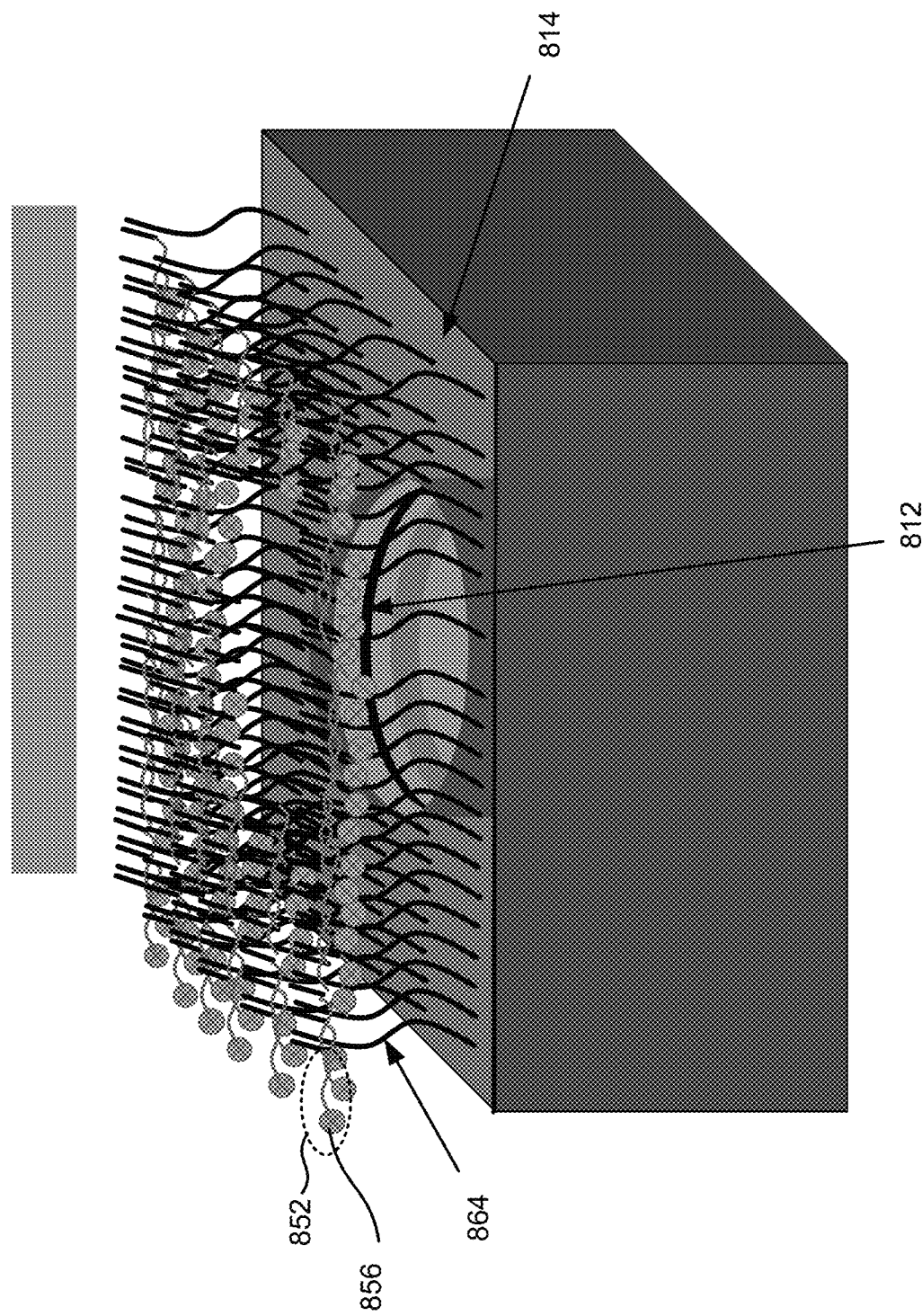

FIG. 8B shows the tunneling junction with nucleic acid molecules attached to adhesion layer 814. The electrical connections, power supplies, reservoir 860, and control system 844 are not shown to better illustrate the attached nucleic acid molecules.

A nucleic acid molecule 864 is attached to adhesion layer 814. Nucleic acid molecule 864 is being hybridized with a nucleotide having label compound 852 including moiety 856. A polymerase may be used to incorporate the nucleotide, but is shown as removed. The polymerase may be one of a set of polymerases. Each polymerase may be connected to one and only one nucleic acid molecule. Each nucleic acid molecules may be connected to one and only one polymerase. The polymerase may be removed from the nucleic acid molecule to facilitate the later bending of the nucleic acid molecule toward insulating layer 812.

Nucleic acid molecule 864 may be one nucleic acid molecule out of a set of nucleic acid molecules attached to adhesion layer 814. The set of nucleic acid molecules attached to adhesion layer 814 may include over 10, over 50, over 100, over 500, or over 1,000 nucleic acid molecules per square micron. Each nucleic acid molecule may have a length. Each nucleic acid molecule of the set of nucleic acid molecules may be attached to a respective point on adhesion layer 814. The distance from the respective point to the opening of the well may be less than the length of the nucleic acid molecule, including less than 0.9, less than 0.8, less than 0.7, less than 0.6, less than 0.5, less than 0.4, less than 0.3, less than 0.2, or less than 0.1 times the length of the nucleic acid molecule. The respective point may be at a respective distance from insulating layer 812. The respective distance may be less than the respective length of the nucleic acid molecule. As a result, the nucleic acid molecule, if oriented in certain ways, can bend to make contact with insulating layer 812 even while the nucleic acid molecule is still attached to the respective point. More specifically, a moiety attached to the nucleic acid molecule would be able to make contact with insulating layer 812. The respective distance may therefore be a distance that does not cross a solid material (e.g., electrodes or adhesion layer).

Figure 8C:
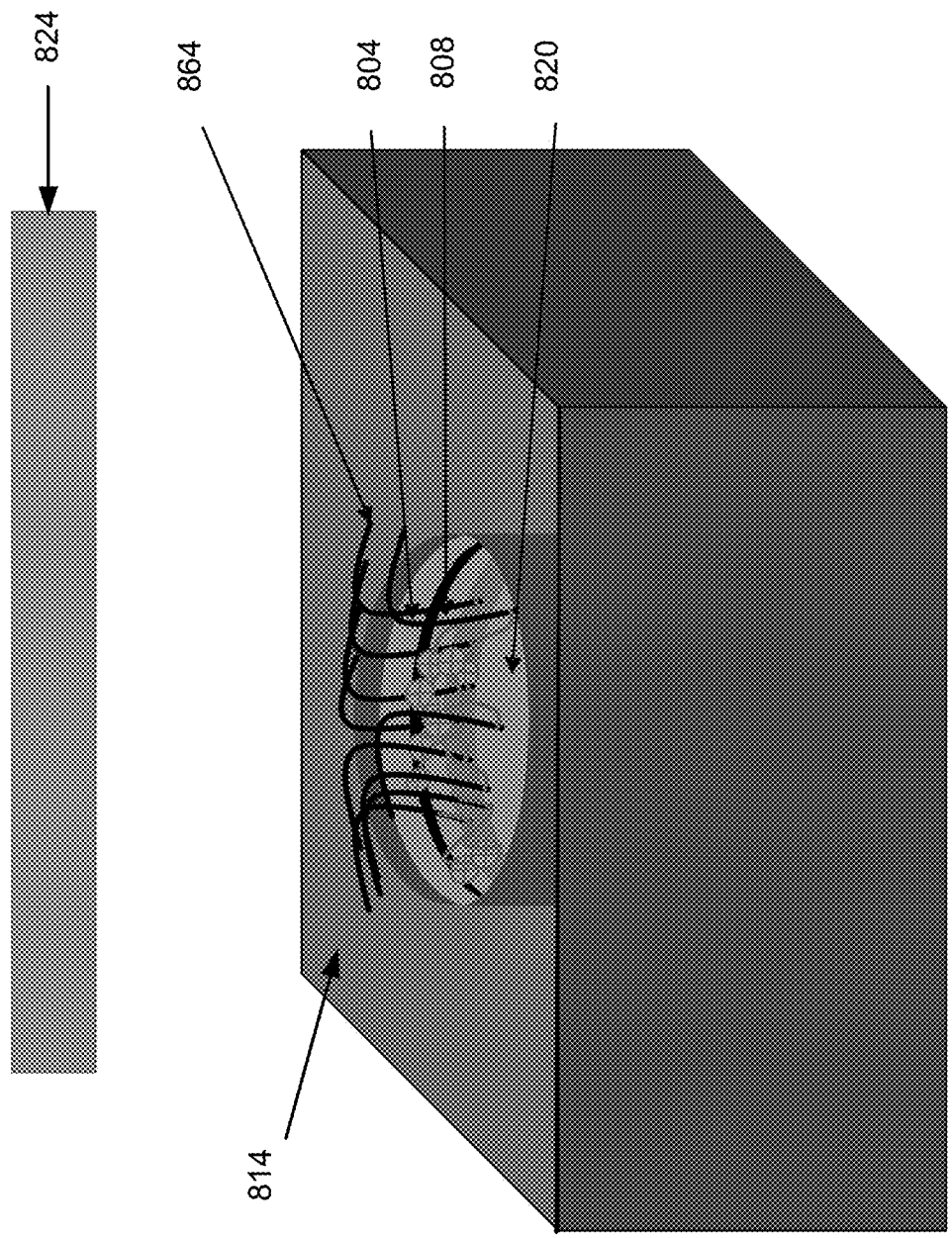

FIG. 8C shows the tunneling junction after a negative potential is applied to second field electrode 824. A positive potential may be applied to first field electrode 820. Nucleic acid molecule 864 stays attached or tethered to adhesion layer 814, but bends into the well toward first field electrode 820. A voltage difference may be applied across first electrode 804 and second electrode 808. Because the moiety has been pushed near the electrodes, current may tunnel from one electrode through the moiety to the other electrode.

The label compound along with the moiety may be removed after a tunneling current is measured and a nucleotide is detected. Another nucleotide with another label compound may be incorporated with a polymerase onto the nascent strand to form a double-stranded nucleic acid molecule. As the nascent strand grows and more of the molecule is a double-stranded molecule, the nucleic acid molecules may become harder to bend toward first field electrode 820.

However, because the surface of adhesion layer 814 would be covered by nucleic acid molecules, some of the molecules may still be positioned so even a smaller bend would bring the moiety close enough to generate a current, including RTN or a tunneling current. The negative potential applied to second field electrode 824 may also be increased as more nucleotides are incorporated to bend the nucleic acid molecules farther.

Figure 9:
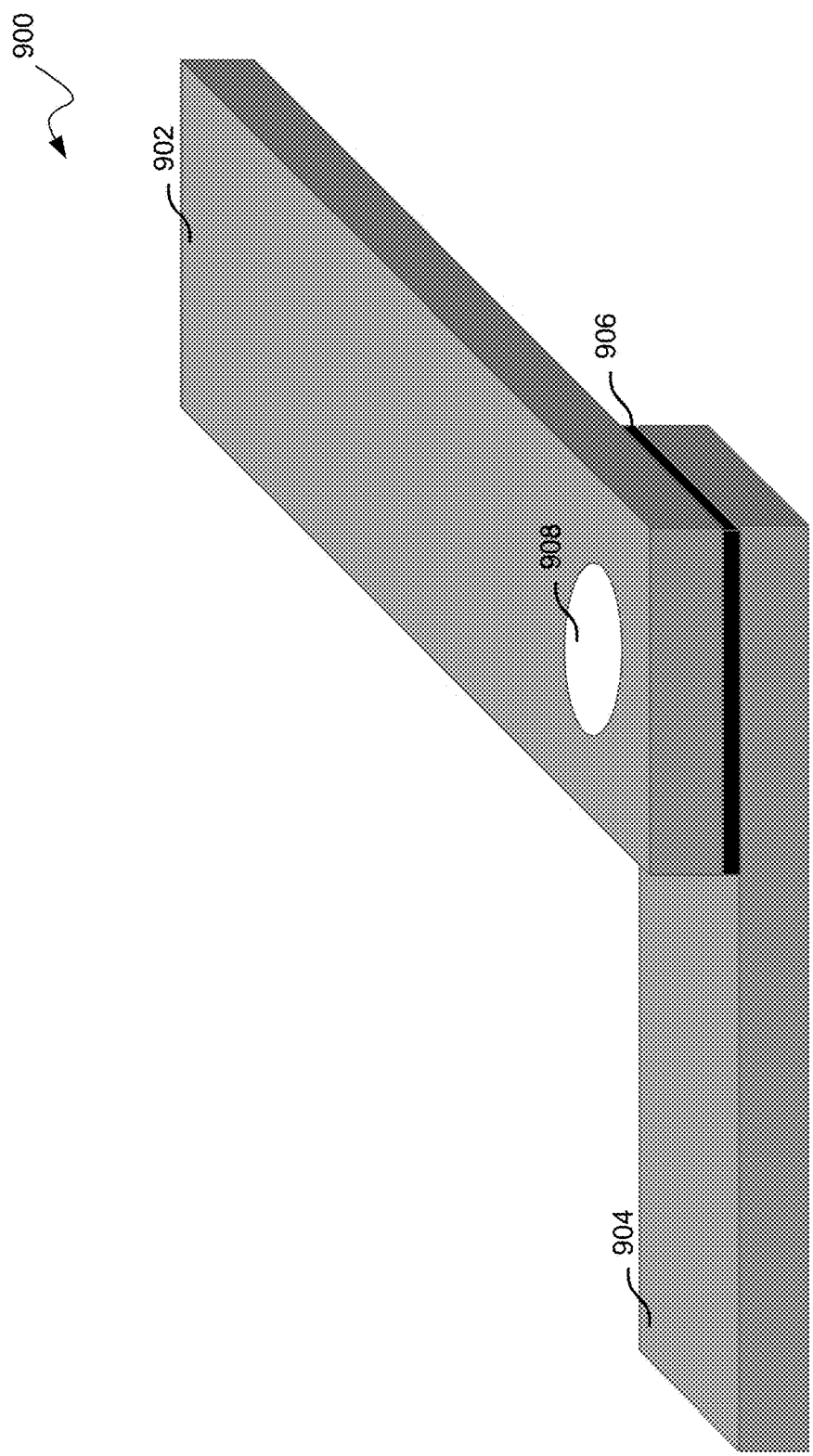
FIG. 9 shows a configuration of electrodes of a tunneling junction according to embodiments of the present invention.

FIG. 9 shows a configuration of the electrodes of a tunneling junction 900. Electrode 902 and electrode 904 are separated by insulating layer 906. Electrode 902 and electrode 904 overlap, and the area of overlap is the area of insulating layer 906. Electrode 902 and electrode 904 may be perpendicular or substantially perpendicular to each other and may each have an area larger than the area of overlap. Well junction opening 908 is shown as a cylinder and may extend through electrode 902, insulating layer 906, and electrode 904. In other embodiments, the well junction opening may be a prism, a polyhedron, or a rectangular solid. The template parent strands may be attached to the top of electrode 902. An electric potential may force the template parent strands toward and/or into junction opening 908.

Figure 10:
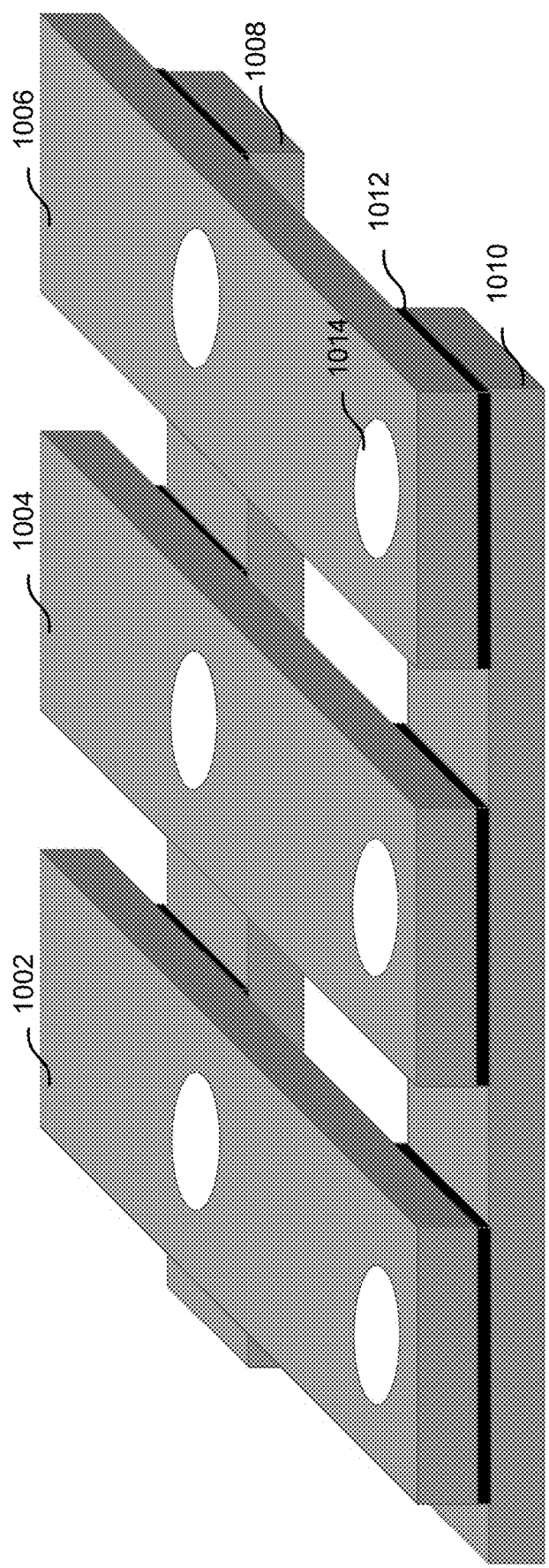
FIG. 10 shows a configuration including a plurality of tunneling junctions according to embodiments of the present invention.

FIG. 10 shows a configuration including a plurality of tunneling junctions. Electrodes 1002, 1004, and 1006 are parallel to each other and perpendicular to electrodes 1008 and 1010. When the electrodes overlap, the electrode are separated by an insulating layer (e.g., insulating layer 1012). A well junction opening (e.g., well junction opening 1014) may be at each area of overlap. The plurality of tunneling junctions may number in the thousands, millions, or billions per square centimeter. Each of the lower electrodes (e.g., electrode 1008 and 1010) may be disposed on the surface of the same substrate. The substrate may include a semiconductor wafer, including a silicon wafer or silicon-on-insulator wafer. Each tunneling junction may be fabricated using semiconductor processing techniques. Each tunneling junction may be identical. A power supply may be in electrical communication with the plurality of tunneling junctions. A meter device or a plurality of meter devices may be in electrical communication with the plurality of tunneling junctions. Electrodes 1002, 1004, and 1006 may be analogous to a word line or a bit line in conventional memory systems, with electrodes 1008 and 1010 being the other type of line.

The tunneling junction may be similar to the tunneling junctions described in U.S. Provisional Application No. 62/654,894, entitled "FABRICATION OF TUNNELING JUNCTIONS WITH NANOPORES FOR MOLECULAR RECOGNITION," filed Apr. 9, 2018, the contents of which are incorporated herein by reference for all purposes.

B. Magnetic Tunneling Junction Systems

Figure 11A:
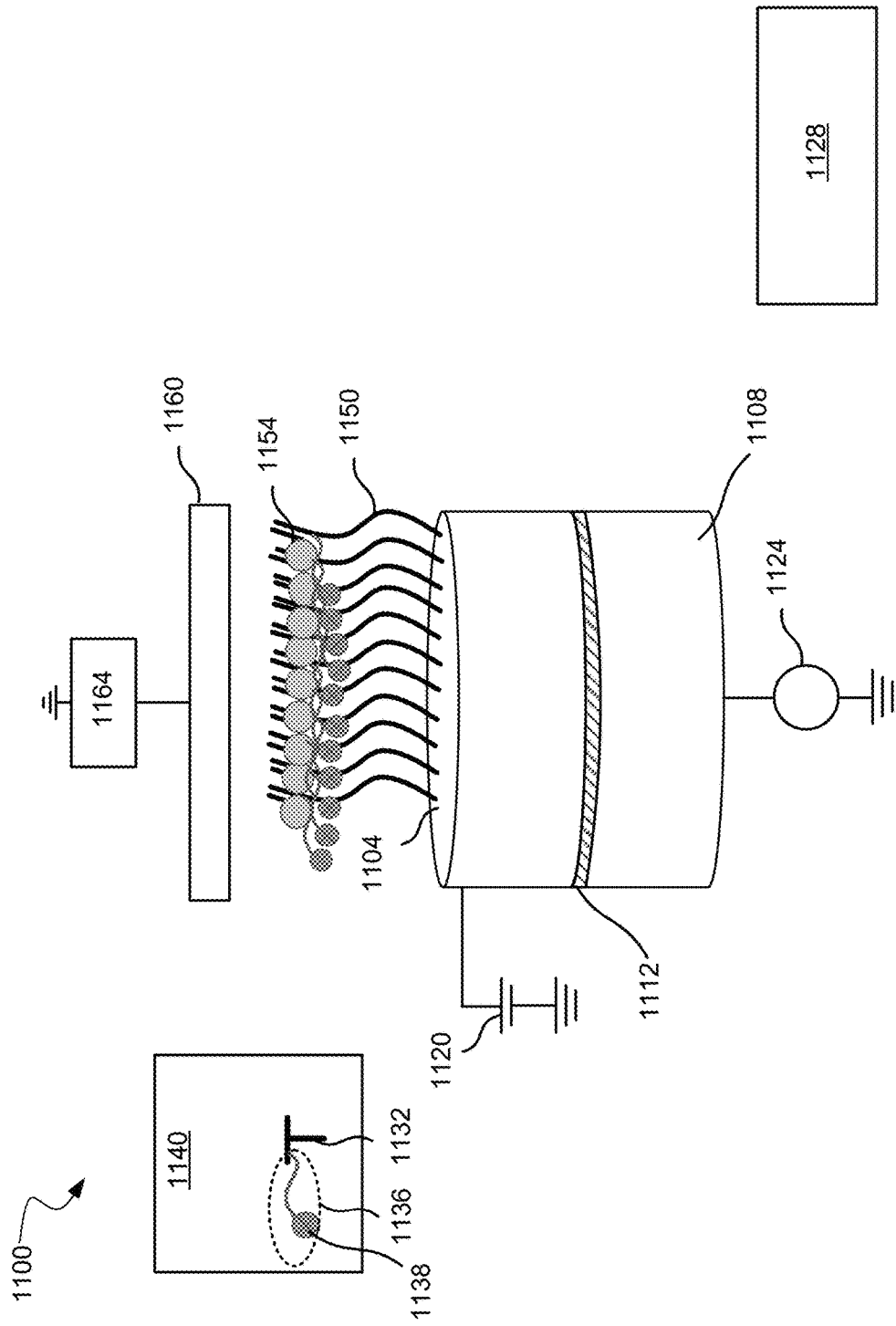
FIGS. 11A and 11B show example systems with a magnetic tunneling junction according to embodiments of the present invention.

FIG. 11A shows an example system 1100. System 1100 may include a tunneling junction. Tunneling junction includes a first ferromagnetic layer 1104, a second ferromagnetic layer 1108, and an insulating layer 1112. The material for the ferromagnetic layers may include cobalt; Co/I/La$_{2/3}$Sr$_{1/3}$MnO$_3$ (LSMO) where I is SrTiO$_3$ (STO), Ce$_{0.69}$La$_{0.31}$, or O$_{1.845}$ (CLO); CoGd; CoPt; CoFe; CoFeB; CoFeTb; iron; Fe$_2$O$_3$; FeOFe$_2$O$_3$; NiOFe$_2$O$_3$; CuOFe$_2$O$_3$; MgOFe$_2$O$_3$; MnBi; Ni; MnSb; MnOFe$_2$O$_3$; Y$_3$Fe$_5$O$_{12}$; MnAs; Gd; Tb; Dy; or EuO. The material for the two ferromagnetic layers may be the same or different. One ferromagnetic layer may be a permanent magnet with one polarity. The other ferromagnetic layer may have its polarity set by an applied magnetic field.

Insulating layer 1112 may include a dielectric material, including alumina (Al$_2$O$_3$), hafnia (HfO$_2$), silicon nitride (Si$_3$N$_4$), silicon oxide (SiO$_2$), glass, quartz, magnesium oxide (MgO), titanium dioxide (TiO$_2$), or zirconium dioxide (ZrO$_2$). Insulating layer 1112 may have a thickness greater than 2 nm. The thickness may be the distance between first ferromagnetic layer 1104 and second ferromagnetic layer 1108. Because operation of the tunnel junction does not require the nucleotide or nucleotides of a nucleic acid molecule to contact both ferromagnetic layers, the width of the insulating layer may be greater than the size of a nucleotide or nucleotides. In addition, the width of the insulating layer may be larger than the size of the moiety as tunneling may still occur even if the moiety is smaller than the gap between the ferromagnetic layers.

A nucleic acid molecule 1150 may be attached to the tunneling junction. Nucleic acid molecule 1150 may be attached to first ferromagnetic layer 1104 directly or indirectly on an adhesion layer on top of first ferromagnetic layer 1104. Nucleic acid polymerase 1154 may be connected to nucleic acid molecule 1150. Nucleic acid polymerase 1154 may elongate a nascent strand being hybridized to a template parent strand. Nucleic acid polymerase 1154 may incorporate a nucleotide with label compound having a moiety.

System 1100 may include field electrode 1160 in electrical communication with power supply 1164. Power supply 1164 may be configured to deliver a negative potential to field electrode 1160 in order to move moieties connected to the nucleic acid molecules to insulating layer 1112. A second, separate field electrode is optional and is not shown. The field electrode configuration may be similar to those in embodiments described for electrical tunneling junctions.

A magnetic tunneling junction does not need a moiety to make contact with any portion of the tunneling junction, as magnetic fields from a moiety can travel through materials along with empty space. The magnetic tunneling junction may be embedded in a non-ferromagnetic material, which may be attached to nucleic acid molecule 1150. The non-ferromagnetic material may include an adhesion layer.

System 1100 may include a power supply 1120. Power supply 1120 may be in electrical communication with at least one of first ferromagnetic layer 1104 and second ferromagnetic layer 1108. Power supply 1120 may apply a voltage to first ferromagnetic layer 1104 and second ferromagnetic layer 1108. Power supply 1120 may be configured to maintain a desired current or a desired voltage. Power supply 1120 may provide voltages from 0 to 3 V, including from 10 mV to 100 mV, from 100 mV to 200 mV, from 200 mV to 300 mV, from 300 mV to 500 mV, from 500 mV to 1 V, from 1 V to 2 V, or from 2 V to 3 V. In some embodiments, power supply 1120 may provide currents of 0 to 10 µA, including from 1 pA to 10 pA, from 10 pA to 100 pA, from 100 pA to 1 nA, 1 nA to 10 nA, from 10 nA to 30 nA, from 30 nA to 100 nA, from 100 nA to 500 nA, from 500 nA to 1 µA, or from 1 µA to 10 µA.

System 1100 may also include a meter device 1124. Meter device 1124 may be configured to measure a value of an electrical or magnetic characteristic through first ferromagnetic layer 1104 and second ferromagnetic layer 1108. Meter device 1124 may be a current meter, a voltage meter, or an oscilloscope. The electrical characteristic may be current or voltage. Meter device 1124 may be a magnetic sensor to measure a magnetic field.

System 1100 may include a control system 1128. Control system 1128 may be in communication with power supply 1120 and meter device 1124. Control system 1128 may also be in communication with control systems that deliver fluid to the tunneling junction. In some embodiments, control system 1128 may include a computer system with a processor and a computer readable medium. The computer readable medium may be store a plurality of instructions. The plurality of instructions, when executed by a process, may cause the processor to perform any method described herein. For example, the plurality of instructions, when executed, may cause the processor to measure the value of the electrical characteristic through the first ferromagnetic layer and the second ferromagnetic layer. The processor may also be caused to compare the value of the electrical characteristic to a reference value of the electrical characteristic. Upon determining the value exceeds the reference value, the processor may further be caused to detect a nucleotide as being hybridized to the template parent strand. Upon determining the value does not exceed the reference value, the processor may further be caused to determine the absence of the nucleotide being hybridized to the template parent strand. A computer system is described in greater detail below. In some embodiments, control system 1128 may include an FPGA or ASIC. The FPGA or ASIC may be configured to perform the plurality of instructions.

System 1100 may include a nucleotide 1132 attached to a label compound 1136. Label compound 1136 may include a moiety 1138. Label compound 1136 may be any label compound described herein. Moiety 1138 may be any moiety described herein.

System 1100 may include a reservoir 1140. Reservoir 1140 may be in fluid communication with the tunneling junction. An injection system may be configured to deliver a liquid from reservoir 1140 to the tunneling junction. Reservoir 1140 may include nucleotide 1132 attached to label compound 1136. Reservoir 1140 may include water. In some embodiments, system 1100 may include a plurality of reservoirs. Each reservoir may include a different liquid to be injected to the tunneling junction. For example, a different reservoir may be used for each of the four types of nucleotide. An additional reservoir may be included to deliver water to rinse the nucleotides from the tunneling junction. Another reservoir may deliver a set of polymerases to the tunneling junction. Each polymerase of the set of polymerases may be configured to elongate a nascent nucleic acid molecule strand that is hybridized to the parent nucleic acid molecule strand.

Figure 11B:
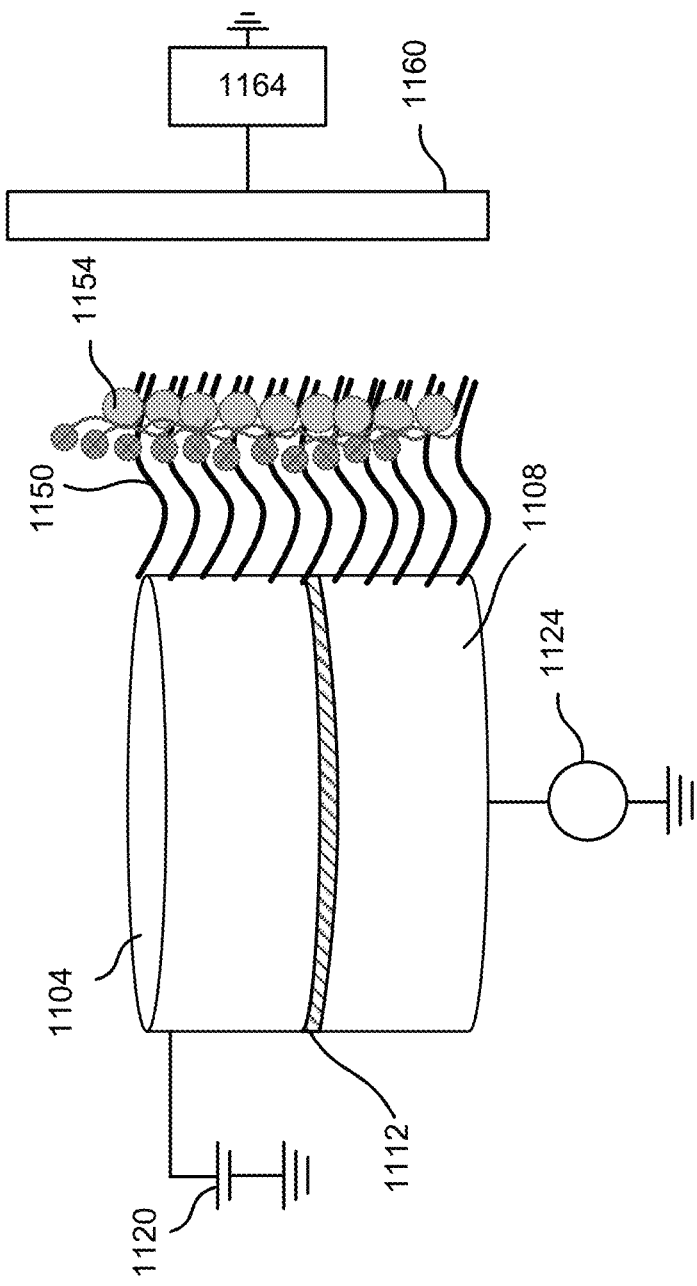

FIG. 11B shows another configuration of how nucleic acid molecules such as nucleic acid molecule 1150 may be attached to the tunneling junction. Nucleic acid molecule 1150 may be attached to an adhesion layer on both first ferromagnetic layer 1104 and second ferromagnetic layer 1108 near insulating layer 1112. In FIG. 11B, the nucleic acid molecules are attached to the cylindrical side of the tunneling junction. Field electrode 1160 may be oriented so that nucleic acid molecule 1150 is between the tunneling junction and field electrode 1160.

A system may also include a plurality of tunneling junctions, similar to the embodiments described in U.S. Provisional Application No. 62/688,257, entitled "TUNNELING JUNCTIONS FOR SEQUENCING," filed Jun. 21, 2018, the contents of which are incorporated herein by reference for all purposes.

C. Systems with Attached Polymerases

Systems may also include systems where the polymerase is tethered to a tunneling junction, similar to the tunneling junctions described in U.S. Provisional Application No. 62/688,257, entitled "TUNNELING JUNCTIONS FOR SEQUENCING," filed Jun. 21, 2018, the contents of which are incorporated herein by reference for all purposes.

Figure 12:
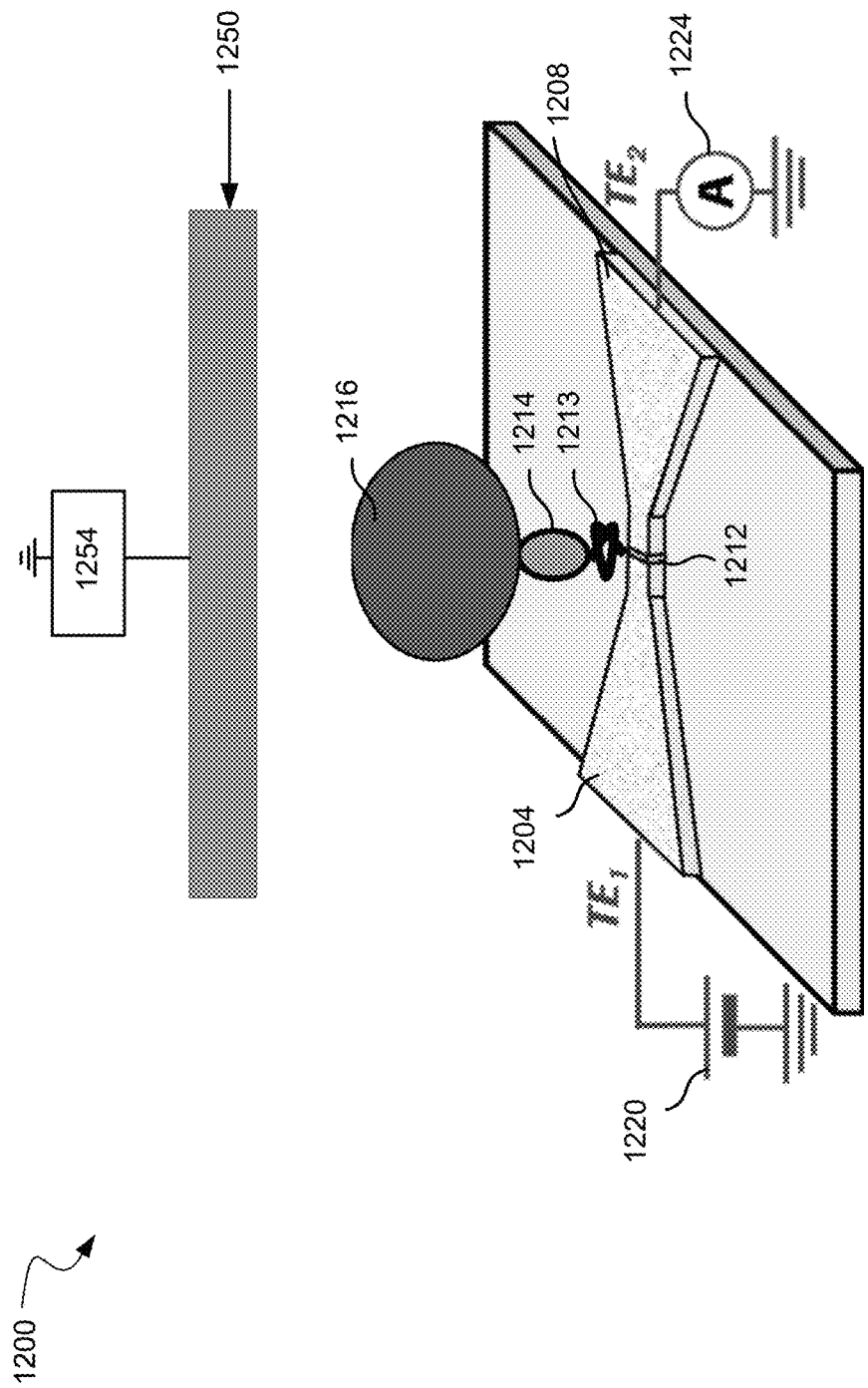
FIG. 12 shows an example system with a tunneling junction with a tethered polymerase according to embodiments of the present invention.

FIG. 12 shows an example system 1200. The figure shows a tunneling junction and a field electrode 1250, but does not show a reservoir with nucleotides attached to label compounds or a computer system to simplify the illustration and focus on field electrode 1250. The reservoir and computer system may be similar to those previously described herein.

System 1200 may include a tunneling junction. Tunneling junction includes a first electrode 1204, a second electrode 1208, and an insulating layer 1212. The electrode may include any metal that has a metal oxide that is chemically stable in the aqueous solution used as the medium for the molecule to be analyzed.

Insulating layer 1212 may include a dielectric material, including alumina ($Al_2O_3$), hafnia ($HfO_2$), silicon nitride ($Si_3N_4$), silicon oxide ($SiO_2$), glass, quartz, magnesium oxide (MgO), titanium dioxide ($TiO_2$), or zirconium dioxide ($ZrO_2$). Insulating layer 1212 may have a thickness greater than 2 nm. The thickness may be the distance between first electrode 1204 and second electrode 1208. Because operation of the tunnel junction does not require the nucleotide or nucleotides of a nucleic acid molecule to contact both electrodes, the width of the insulating layer may be greater than the size of a nucleotide or nucleotides. In addition, the width of the insulating layer may be larger than the size of the moiety as tunneling may still occur even if the moiety is smaller than the gap between the electrodes.

The tunneling junction may be oriented laterally, such that the tunneling direction is substantially parallel to the surface of a substrate contacting the first electrode and the second electrode. The direction of the elongation of the nascent strand may be parallel to the surface of the substrate. The insulating layer may have a longitudinal axis that is orthogonal to the substrate. Examples of laterally-oriented tunneling junctions are described in U.S. Patent Publication No. 2018/0031523 A1, the contents of which are incorporated herein by reference for all purposes.

A nucleic acid polymerase 1216 may be attached to the tunneling junction by a tether compound formed by tether compound 1213 and compound 1214. Tether compound 1213 may include SpyTag, and compound 1214 may include SpyCatcher. Nucleic acid polymerase 1216 may be attached to the tunneling junction at insulating layer 1212. Nucleic acid polymerase 1216 may also be attached to the tunneling junction at first electrode 1204 or second electrode 1208. A compound or compounds may tether nucleic acid polymerase 1216 to insulating layer 1212. For example, hydroquinone, SpyTag, or SpyCatcher may be used to tether nucleic acid polymerase 1216 to insulating layer 1212. Nucleic acid polymerase 1216 may be configured to elongate a nascent strand. The nascent strand may be hybridized to a template parent strand.

System 1200 may also include a meter device 1224. Meter device 1224 may be configured to measure a value of an electrical characteristic through first electrode 1204 and second electrode 1208. Meter device 1224 may be a current meter, a voltage meter, or an oscilloscope. The electrical characteristic may be current or voltage.

System 1200 may include field electrode 1250. Field electrode 1250 may be similar to second field electrode 824. Field electrode 1250 may be in electrical communication with power supply 1254. Power supply 1254 may be similar to power supply 828. Field electrode 1250 may be positioned so that polymerase 1216 is between field electrode 1250 and insulating layer 1212. Power supply 1254 may deliver a negative voltage to field electrode 1250. The negative voltage results in an electric field that may propel any nucleic acid molecule being hybridized by polymerase 1216 toward insulating layer 1212. In this manner, a nucleotide with a label compound may generate a tunneling current or direct current between first electrode 1204 and second electrode 1208. Another field electrode providing a ground or a positive voltage is not shown in FIG. 12. This field electrode may be similar to first field electrode 820.

While FIG. 12 shows an electrical tunneling junction, a field electrode may be used with a magnetic tunneling junction to which a polymerase is tethered. The field electrode would operate in a similar manner and propel a template parent strand with a nucleotide and moiety toward the tunneling junction.

Methods using a tunneling junction with a tethered polymerase may include an additional step of applying a voltage to a field electrode. The voltage may move a template parent strand and a moiety of a label compound attached to an incorporated nucleotide closer to insulating layer 1212.

V. Example Systems

Figure 13:
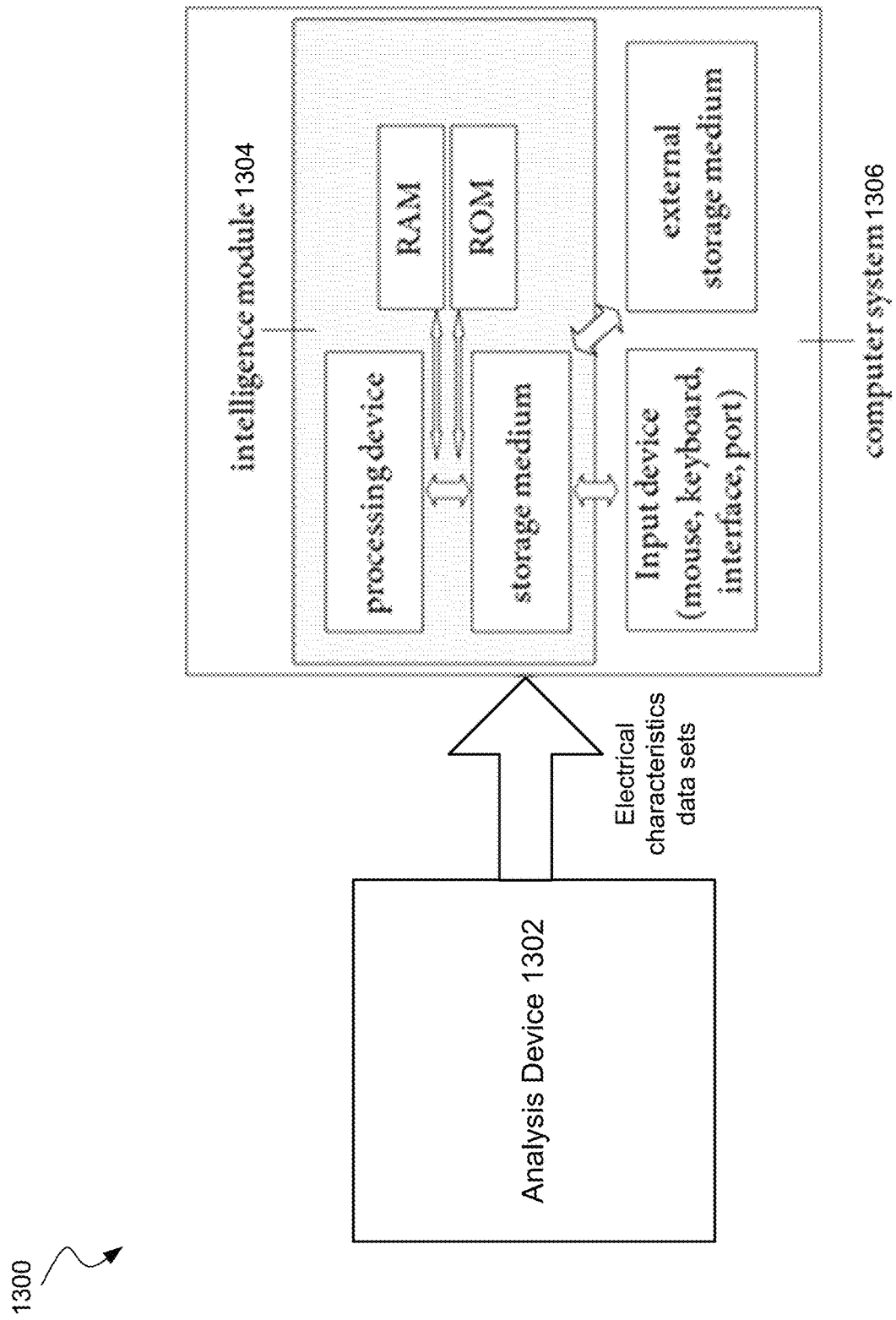
FIG. 13 shows an analysis system according to embodiments of the present invention.

FIG. 13 shows an exemplary analysis system. The system depicted in FIG. 13 comprises an analysis device 1302 and an intelligence module 1304 that is part of the computer system 1306. Analysis device 1302 may include system 800, system 1100, or any system described herein. Computer system 1306 may include parts or all of computer system 10. The data sets (electrical characteristics data sets) are transferred from the analysis device 1302 to the intelligence module 1304 or vice versa via a network connection or a direct connection. The data sets may for example be processed to identify nucleotides. The identification steps may be implemented by software stored on the hardware of computer system 1306. The data sets may be processed by computer code running on the processor and being stored on the storage device of the intelligence module and after processing transferred back to the storage device of the analysis module, where the modified data may be displayed on a displaying device. In some embodiments, the intelligence module may also be implemented in the analysis device.

Figure 14:
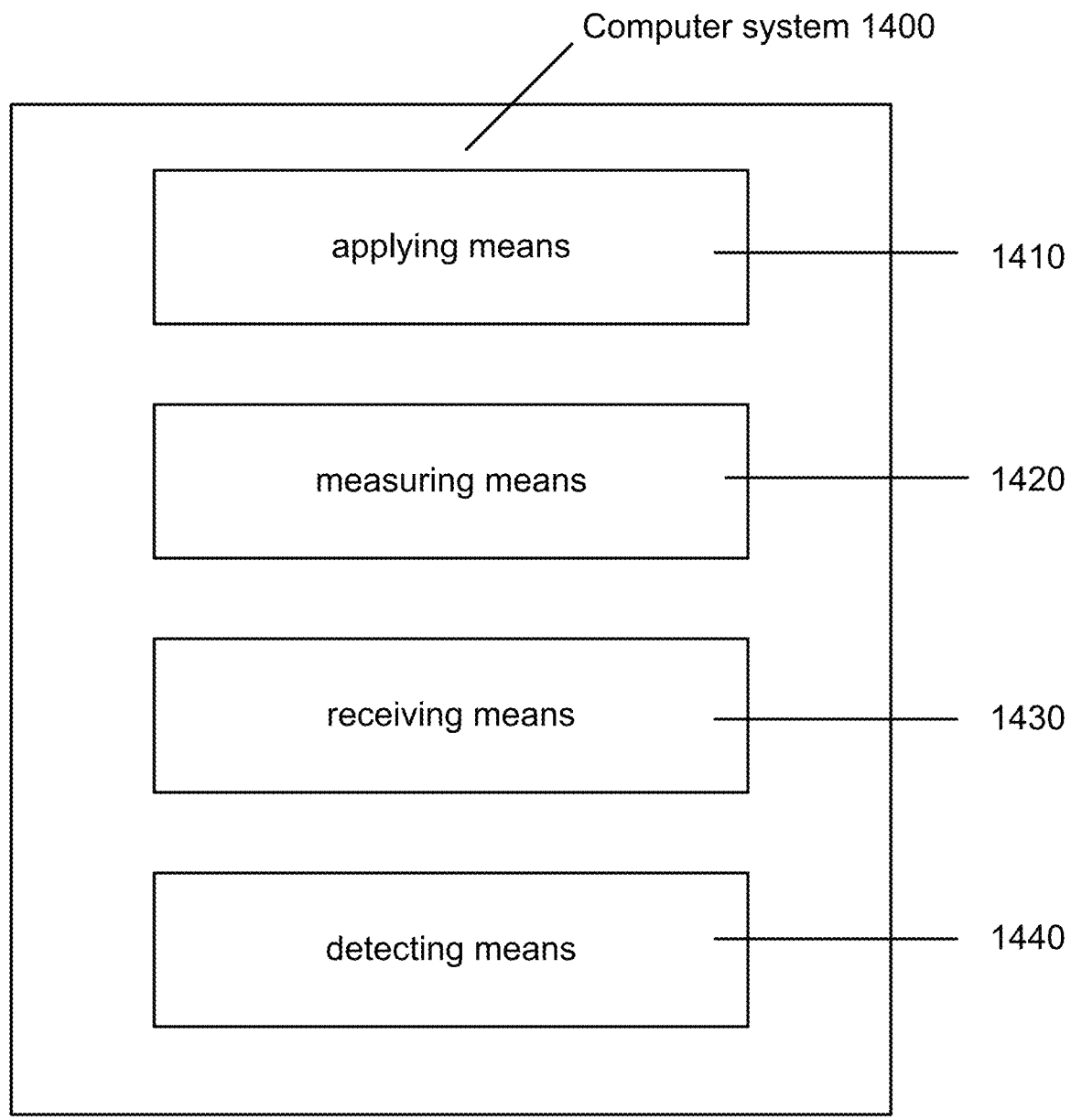
FIG. 14 shows a computer system according to embodiments of the present invention.

FIG. 14 shows that computer system 1400 may comprise applying means 1410, which may include, for example, applying a voltage across a first electrode and a second electrode separated by an insulating layer. Computer system 1400 may be a field-programmable gate array (FPGA) or application-specific integrated circuit (ASIC). Computer system 1400 may also include measuring means 1420, which may include measuring a value of an electrical characteristic through the first electrode and the second electrode. Computer system 1400 may further include receiving means, which may include receiving the value of an electrical characteristic from an analysis system. Computer system 1400 may also include detecting means, which may include, for example, detecting a nucleotide as being hybridized to the template parent strand using the value of the electrical characteristic.

Figure 15:
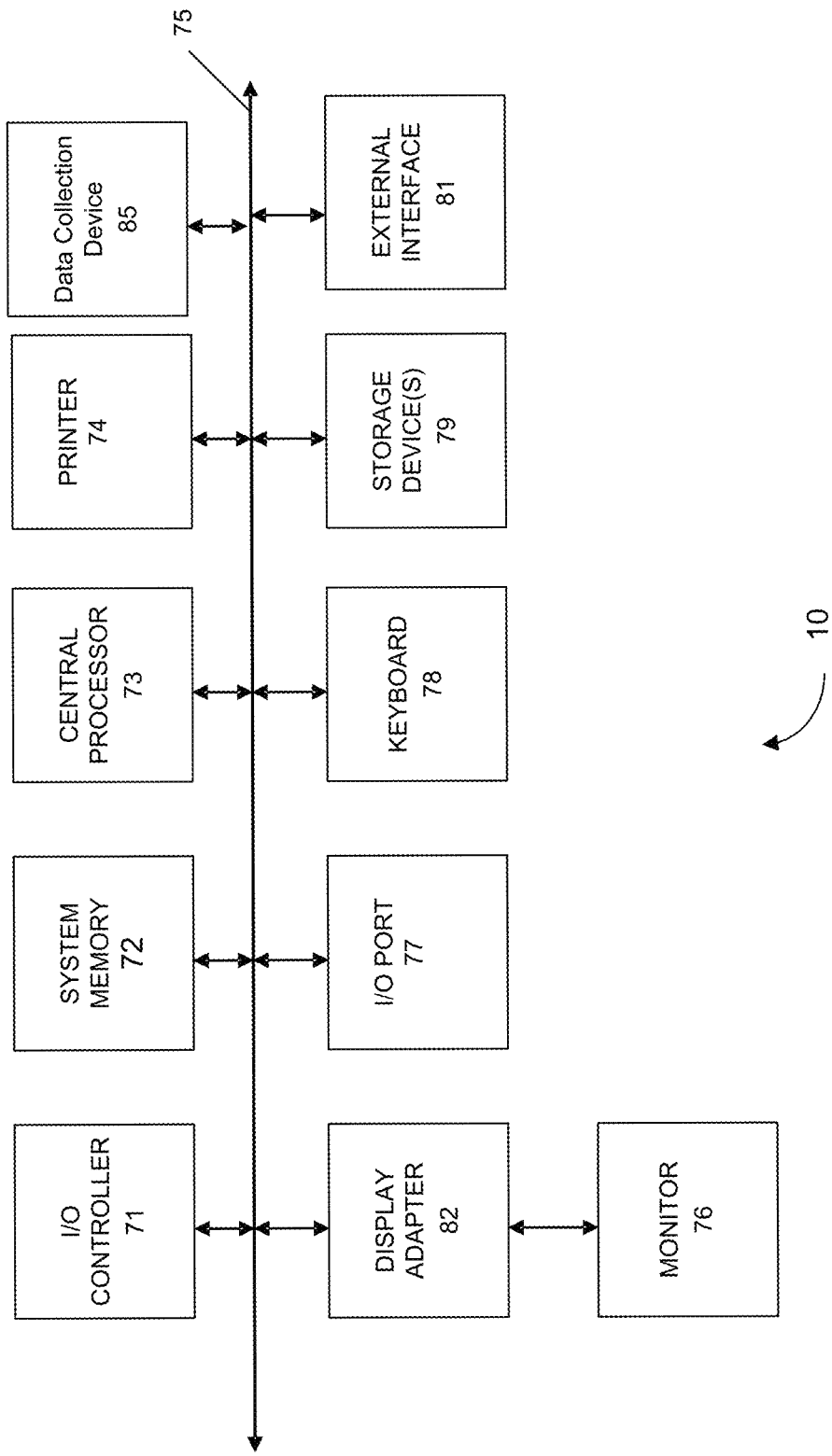
FIG. 15 shows a computer system according to embodiments of the present invention.

Any of the computer systems mentioned herein may utilize any suitable number of subsystems. Examples of such subsystems are shown in FIG. 15 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. Computer system 10 may be a field-programmable gate array (FPGA) or application-specific integrated circuit (ASIC).

The subsystems shown in FIG. 15 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®, Thunderbolt). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the moiety" includes reference to one or more moieties and equivalents thereof known to those skilled in the art, and so forth. The invention has now been described in detail for the purposes of clarity and understanding. However, it will be appreciated that certain changes and modifications may be practice within the scope of the appended claims.

The invention claimed is:

1. A method of determining a sequence of a nucleic acid using a sequencing device, the method comprising:
connecting a polymerase to a template parent strand attached to the sequencing device, the sequencing device comprising a first ferromagnetic material and a second ferromagnetic material separated by an insulating layer, wherein the first ferromagnetic material, the second ferromagnetic material, and the insulating layer form a tunneling junction;
adding a set of nucleotides to the sequencing device, each nucleotide of the set of nucleotides attached to a respective label compound, wherein each nucleotide attached to the respective label compound has a structure represented by N—X—S-M, where N is the nucleotide, X is a cleavable linker, S is a spacer, and M is a moiety, wherein the tunneling junction is a magnetic tunneling junction and the moiety is selected from the group consisting of a ferromagnetic material and a superparamagnetic material;
elongating a nascent strand using the polymerase connected to the template parent strand, wherein the elongating includes the polymerase incorporating a first nucleotide of the set of nucleotides into the nascent strand via hybridization to the template parent strand;
applying an electric potential to move the template parent strand and a first moiety of a first label compound attached to the first nucleotide closer to the insulating layer while the template parent strand is attached to the sequencing device;
measuring a value of an electrical characteristic or a magnetic characteristic through the first ferromagnetic material, the first moiety, and the second ferromagnetic material while applying the electric potential; and
detecting the first nucleotide as being hybridized to the template parent strand using the value of the electrical characteristic or the magnetic characteristic.

2. The method of claim 1, wherein:
the applying the electric potential comprises applying a negative voltage to an electrode, and
the electrode disposed such that the nascent strand is between the electrode and the insulating layer.

3. The method of claim 1, wherein:
the template parent strand is attached to an adhesion layer, and
the adhesion layer contacts the first ferromagnetic material.

4. The method of claim 3, wherein the adhesion layer comprises silicon dioxide.

5. The method of claim 1, wherein:
the first moiety contacts the first ferromagnetic material and the second ferromagnetic material, the measuring the value of the electrical characteristic or the magnetic characteristic comprises measuring the electrical characteristic, and the electrical characteristic is a current.

6. The method of claim 1, wherein:

the template parent strand is one template parent strand of a set of template parent strands, the polymerase is one polymerase of a set of polymerases, the method further comprising:

attaching the set of template parent strands to the sequencing device, connecting the set of polymerases to the set of template parent strands, wherein:

each polymerase of the set of polymerases is connected to only one template parent strand of the set of template parent strands, and each template parent strand of the set of template parent strands is connected to only one polymerase of the set of polymerases.

7. The method of claim 6, wherein:

the set of template parent strands is a first set of template parent strands, the method further comprising:

forming the first set of template parent strands by bridge amplifying a second set of template parent strands attached to the sequencing device.

8. The method of claim 1, further comprising attaching a primer to the template parent strand before connecting the polymerase to the template parent strand.

9. The method of claim 1, wherein the applying the electric potential moves the first moiety of the first label compound to contact the first ferromagnetic material and the second ferromagnetic material.

10. The method of claim 1, the method further comprising:

applying a voltage across the first ferromagnetic material and the second ferromagnetic material, wherein:

the applying the electric potential moves the first moiety of the first label compound to a distance where a current can tunnel from the first ferromagnetic material through the first moiety to the second ferromagnetic material when the voltage is applied.

* * * * *